(12) United States Patent
Mariottini et al.

(10) Patent No.: US 10,755,817 B2
(45) Date of Patent: Aug. 25, 2020

(54) SYSTEMS, APPARATUSES AND METHODS FOR PREDICTING MEDICAL EVENTS AND CONDITIONS REFLECTED IN GAIT

(71) Applicant: Board of Regents, The University of Texas System, Austin, TX (US)

(72) Inventors: Gian-Luca Mariottini, Arlington, TX (US); Aaron N. Staranowicz, Carlsbad, CA (US); Christopher T. Ray, Mansfield, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 739 days.

(21) Appl. No.: 14/946,890

(22) Filed: Nov. 20, 2015

(65) Prior Publication Data

US 2016/0147959 A1    May 26, 2016

Related U.S. Application Data

(60) Provisional application No. 62/082,360, filed on Nov. 20, 2014.

(51) Int. Cl.
*G16H 50/20* (2018.01)

(52) U.S. Cl.
CPC .................................. *G16H 50/20* (2018.01)

(58) Field of Classification Search
None
See application file for complete search history.

(56) References Cited

U.S. PATENT DOCUMENTS

| | | | |
|---|---|---|---|
| 6,383,150 B1 * | 5/2002 | Stewart | A61B 5/4023 600/300 |
| 7,612,681 B2 | 11/2009 | Azzaro et al. | |
| 2004/0199361 A1 * | 10/2004 | Lu | G05B 19/41875 702/183 |
| 2007/0021689 A1 | 1/2007 | Stergiou et al. | |

(Continued)

FOREIGN PATENT DOCUMENTS

CN    103598889    * 2/2014    ............... A61B 5/11

OTHER PUBLICATIONS

Lai, Kevin, Liefeng Bo, Xiaofeng Ren, and Dieter Fox. "A large-scale hierarchical multi-view rgb-d object dataset." In Robotics and Automation (ICRA), 2011 IEEE International Conference on, pp. 1817-1824. IEEE, 2011. (Year: 2011).*

(Continued)

*Primary Examiner* — Alexey Shmatov
*Assistant Examiner* — Casey R. Garner
(74) *Attorney, Agent, or Firm* — Thomas | Horstemeyer, LLP

(57) ABSTRACT

A system for predicting medical events and conditions that are reflected in gait may include a data capture subsystem configured to capture data pertaining to a position and/or motion of a patient, a data analysis and outcome generation subsystem configured to analyze the captured data and to generate output pertaining to a likelihood of the patient experiencing a medical event or medical condition, and a user interface subsystem configured to provide the output to a user, e.g., healthcare provider, and to receive feedback from the user. Methods for predicting medical events and conditions reflected in gait are also provided.

17 Claims, 9 Drawing Sheets

(56) References Cited

U.S. PATENT DOCUMENTS

| | | | | |
|---|---|---|---|---|
| 2007/0275830 | A1* | 11/2007 | Lee | A61B 5/1038 482/54 |
| 2008/0108913 | A1* | 5/2008 | Lengsfeld | A61B 5/1038 600/595 |
| 2008/0186189 | A1* | 8/2008 | Azzaro | A61B 5/1113 340/573.7 |
| 2009/0232353 | A1* | 9/2009 | Sundaresan | G06K 9/00342 382/103 |
| 2011/0099195 | A1* | 4/2011 | Patwardhan | G06F 17/3084 707/769 |
| 2013/0178304 | A1* | 7/2013 | Chan | A63B 69/36 473/266 |
| 2014/0153794 | A1* | 6/2014 | Varaklis | A61B 5/1124 382/128 |
| 2014/0376876 | A1* | 12/2014 | Bentley | G06F 16/7837 386/227 |
| 2016/0081594 | A1* | 3/2016 | Gaddipati | A61B 5/1113 600/595 |

OTHER PUBLICATIONS

Wang, Fang, Erik Stone, Marjorie Skubic, James M. Keller, Carmen Abbott, and Marilyn Rantz. "Toward a passive low-cost in-home gait assessment system for older adults." IEEE journal of Biomedical and Health Informatics 17, No. 2 (2013): 346-355. (Year: 2013).*

Kang, Hyun Gu, and Jonathan B. Dingwell. "Separating the effects of age and walking speed on gait variability." Gait & posture 27, No. 4 (2008): 572-577. (Year: 2008).*

Aaron Staranowicz, Garrett R. Brown, Fabio Morbidi, Gian-Luca Mariottini, "Easy-to-Use and Accurate Calibration of RGB-D Cameras from Spheres," Proc. 6th Pacific-Rim Symposium on Image and Video Technology, PSIVT 2013, LNCS 8333, Oct. 2013, pp. 265-278, Springer-Verlag, Berlin.

Chien-Wen-Cho, Wen-Hung Chao, Sheng-Huang Lin, You-Yin Chen, "A vision-based analysis system for gait recognition in patients with Parkinson's disease," Expert Systems with Applications, 2009, pp. 7033-7039, vol. 36, Elsevier.

Fang Wang, Marjorie Skubic, Marilyn Rantz, Paul E. Cuddihy, "Quantitative Gait Measurement with Pulse-Doppler Radar for Passive In-home Gait Assessment," IEEE Transactions on Biomedical Engineering, Sep. 2014, pp. 2434-2443, vol. 61, No. 9, IEEE.

Heba Lakany, "Extracting a diagnostic gait signature," Pattern Recognition: The Journal of the Pattern Recognition Society, 2008, pp. 1627-1637, vol. 41, Elsevier.

Joonbum Bae, Kyoungchul Kong, Nancy Byl, Masayoshi Tomizuka, "A Mobile Gait Monitoring System for Abnormal Gait Diagnosis and Rehabilitation: A Pilot Study for Parkinson Disease Patients," Journal of Biomechanical Engineering, Apr. 2011, 11 pgs., vol. 133, ASME.

Slawomir Chandzlik, Jan Piecha, "The Body Balance Measures for Neurological Disease Estimation and Classification," Journal of Medical Informatics & Technologies, 2003, 8 pgs., vol. 6.

Aaron Staranowicz, Gian-Luca Mariottini, "Evaluating the Accuracy of a Mobile Kinect-based Gait-Monitoring System for Fall Prediction," Proc. Int. Conf. on Pervasive Technologies Related to Assistive Environments, PETRA 2013, May 2013, 4 pgs., ACM.

Jan Piecha, "Gait Motor Disturbances in Neurological Diseases Diagnosis," Computer Recognition Systems 2, ASC 45, 2007, pp. 653-662, Springer-Verlag, Berlin.

* cited by examiner

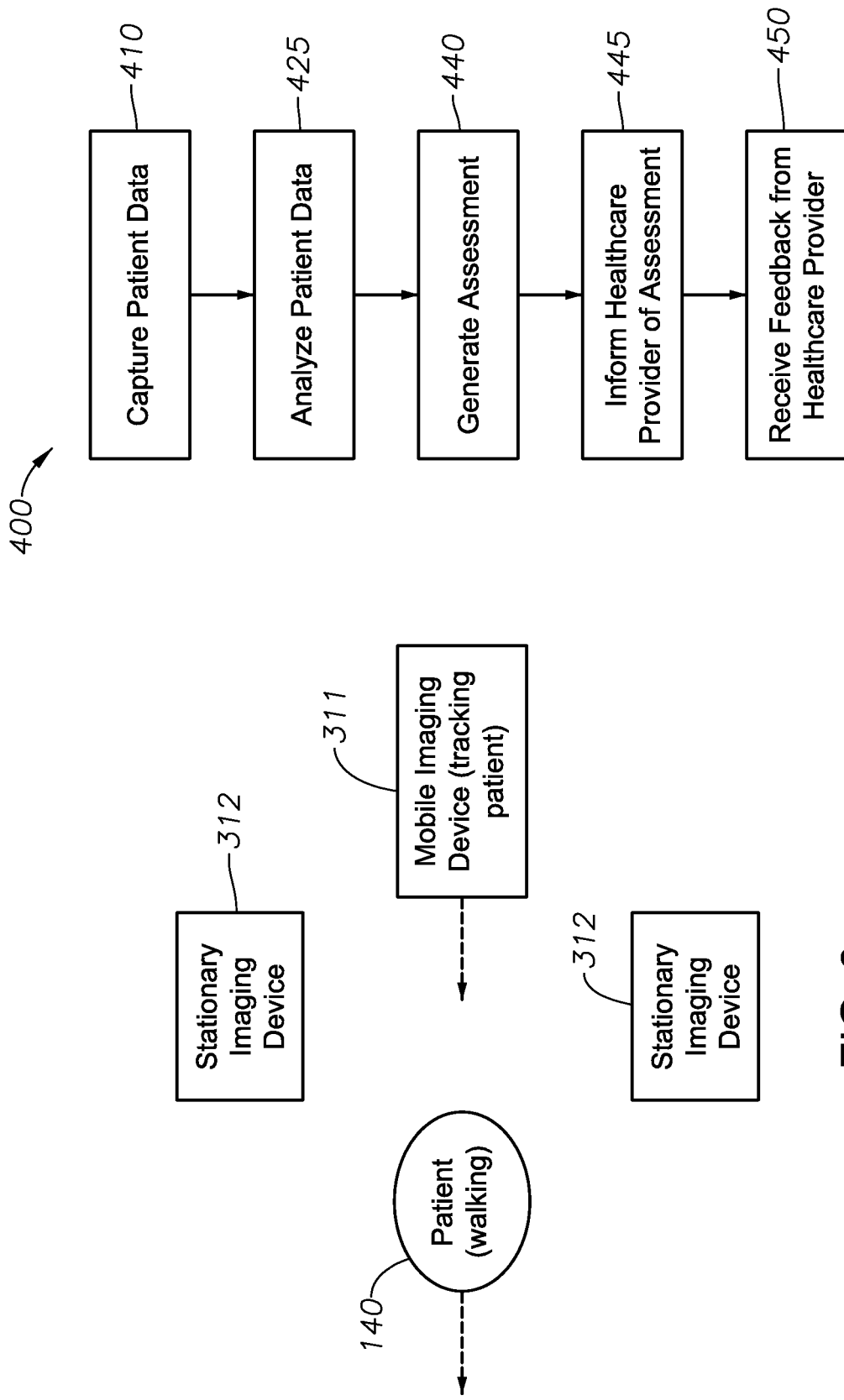

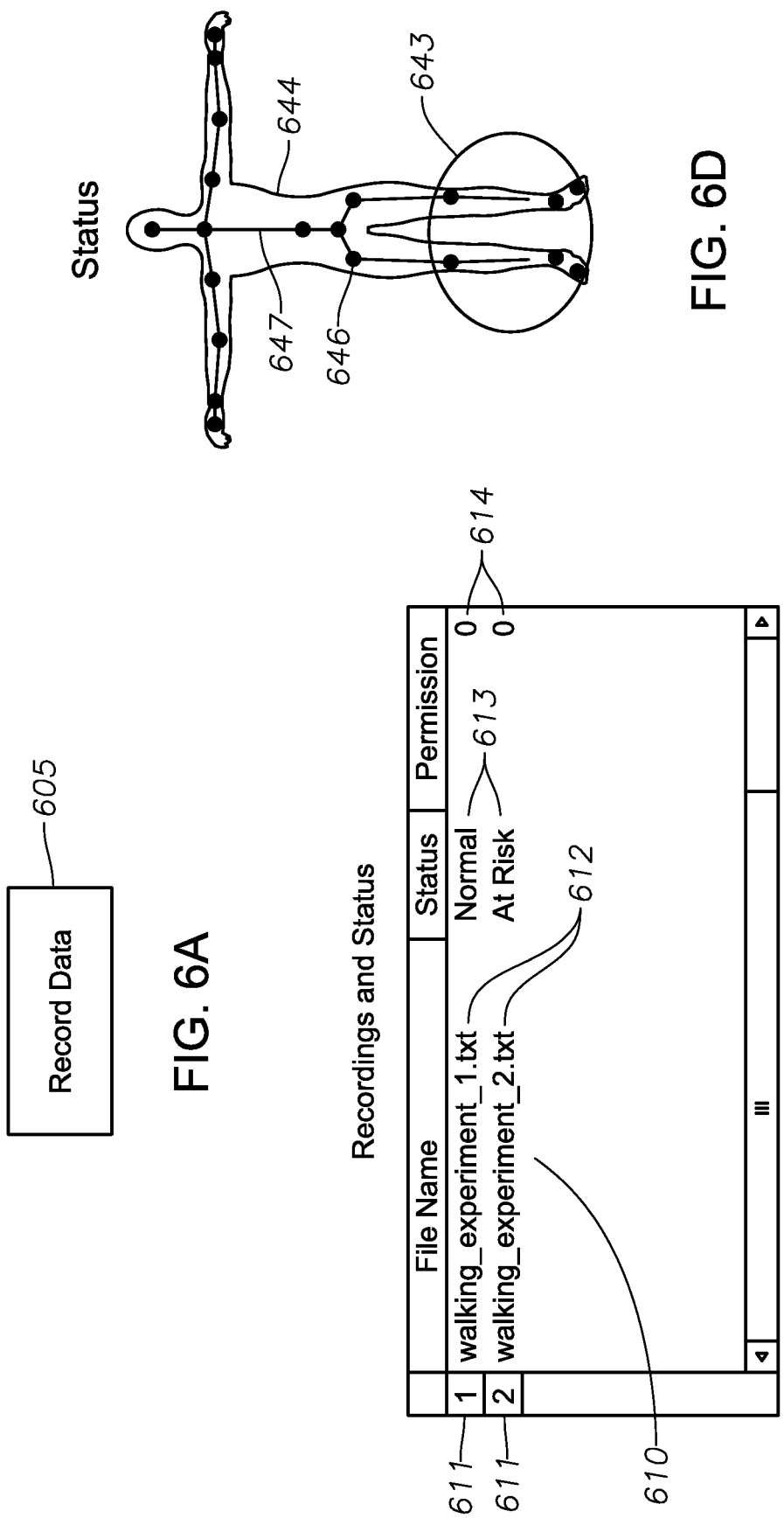

SYSTEMS, APPARATUSES AND METHODS FOR PREDICTING MEDICAL EVENTS AND CONDITIONS REFLECTED IN GAIT

CROSS-REFERENCE TO RELATED APPLICATIONS

This application claims the benefit of the filing date of U.S. Provisional Patent Application No. 62/082,360, filed on Nov. 20, 2014, by the inventors of this application, and incorporated herein by reference.

STATEMENT REGARDING FEDERALLY SPONSORED RESEARCH

Not applicable.

FIELD OF THE INVENTION

This disclosure relates generally to systems, apparatuses and methods for predicting medical events and conditions that are reflected in gait.

DESCRIPTION OF THE RELATED ART

Falls pose a serious health risk to the elderly. Certain neurodegenerative diseases and other medical conditions, which pose serious health risks to the population at large, resemble falls in that signs or precursors of both may be manifested in an individual's gait or body motion. Detection of early warning of signs of a fall or neurodegenerative condition may permit effective proactive medical intervention and hence mitigation of adverse health effects upon the affected individuals. Existing systems that measure an individual's motion and attempt to predict falls suffer from various disadvantages. For example, some systems are inaccurate due to accumulated error in the acquired gait data that may result from, e.g., an insufficient number of cameras (recording patient motion) or cameras which are not mobile. Some systems are burdensome for the patient being monitored because the patient is required to wear (e.g., infrared reflective) markers that are used to measure the patient's motion. Some systems are impractical for in-home use by the average individual for various reasons: e.g., the systems require involvement of a technical expert, e.g., to install or calibrate motion sensors; the system's cost is exorbitant for the average in-home user, e.g., systems using the Vicon™ motion capture system; the systems have limited data capture volume and so cannot monitor an individual moving about engaging in everyday activities. Accordingly, there is a need for a system for predicting medical events and conditions reflected in gait that is less vulnerable to the above-mentioned drawbacks.

SUMMARY OF THE INVENTION

Embodiments of the present invention provides systems, apparatuses, and methods for predicting medical events and conditions reflected in gait, that represent improvements with respect to at least some of the above-mentioned drawbacks in the prior art.

According to a first aspect of the invention, there is provided a system for predicting medical events and conditions reflected in gait. The system includes a data capture subsystem configured to capture data pertaining to a position and/or motion of a patient, a data analysis subsystem configured to analyze the captured data and to generate output pertaining to a likelihood of the patient experiencing a medical event or medical condition, and a user interface subsystem configured to provide the output to a user and to receive feedback from the user.

According to a second aspect of the invention, there is provided a method for predicting medical events and conditions reflected in gait. The method includes capturing data pertaining to a position and/or motion of a patient, analyzing the captured data and generating output pertaining to a likelihood of the patient experiencing a medical event or medical condition, and providing the output to a user and receiving feedback from the user.

Other systems, apparatuses, and methods are also provided.

BRIEF DESCRIPTION OF THE DRAWINGS

It being understood that the figures presented herein should not be deemed to limit or define the subject matter claimed herein, the instant disclosure may be understood by reference to the following description taken in conjunction with the accompanying drawings, in which:

FIG. 3 is a block diagram illustrating a data capture subsystem of a system for predicting medical events and conditions that are reflected in gait, according to some embodiments;

FIG. 4 is a flow chart illustrating, at a top level, a method for predicting medical events and conditions that are reflected in gait, according to some embodiments;

FIGS. 6A-6E illustrate exemplary screenshots of a user interface for a system and method for predicting medical events and conditions that are reflected in gait, according to some embodiments;

DETAILED DESCRIPTION OF DISCLOSED EMBODIMENTS

Figure 1:
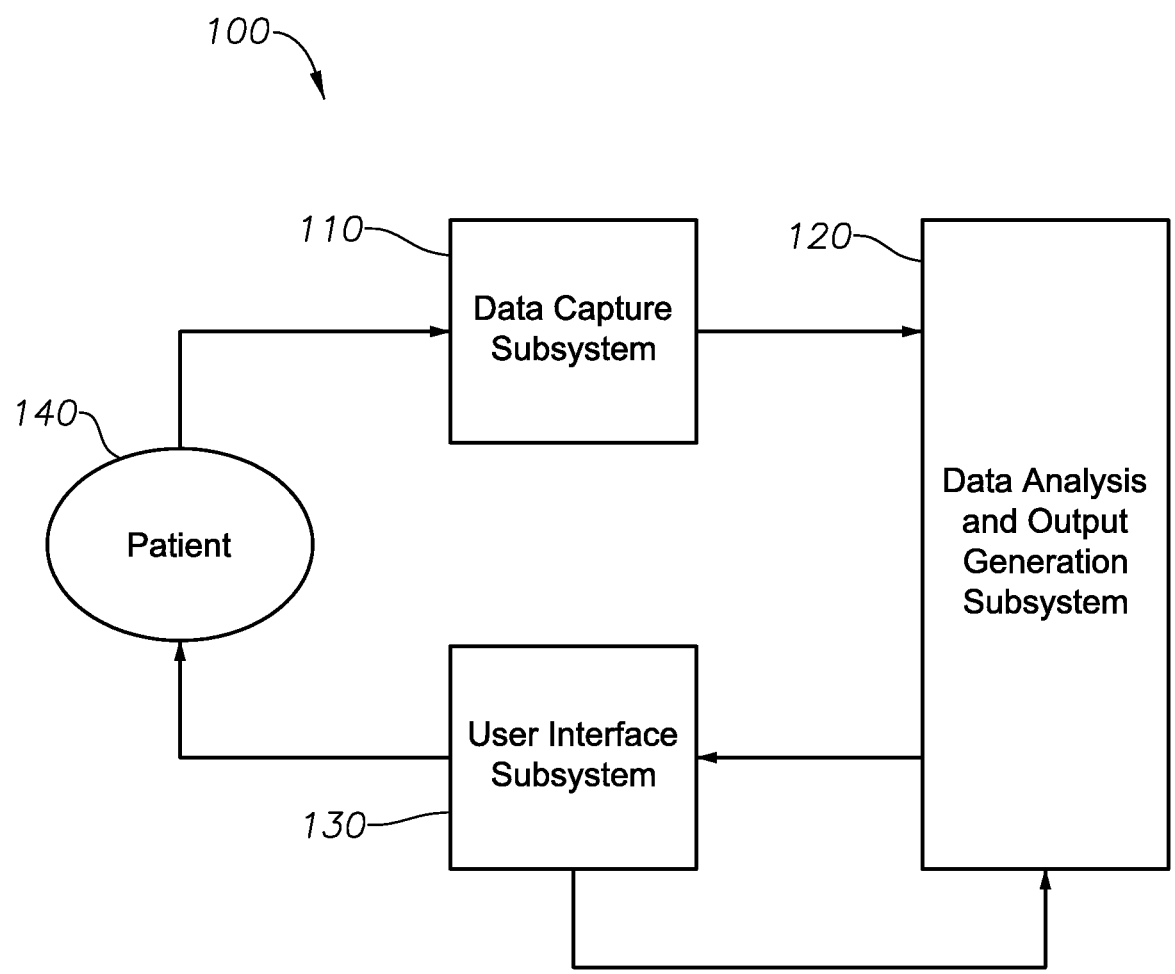
FIG. 1 is a block diagram illustrating, at a top level, a system for predicting medical events and conditions that are reflected in gait, according to some embodiments.

While various embodiments are described herein, it should be appreciated that the present invention encompasses many inventive concepts that may be embodied in a wide variety of contexts. Thus, the following detailed description of exemplary embodiments, read in conjunction with the accompanying drawings, is merely illustrative and is not to be taken as limiting the scope of the invention. Rather, the scope of the invention is defined by the appended claims and equivalents thereof.

Illustrative embodiments of the invention are described below. In the interest of clarity, not all features of an actual implementation are necessarily described for each embodiment disclosed in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide for a system for predicting medical events (e.g., falls or similar events) and conditions that are reflected in gait. The phrase "medical events and conditions that are reflected in gait" may be explained as follows. Certain medical events and conditions are associated (at least in some instances) with signs that manifest themselves in the gait of an individual. These signs indicate the likely future occurrence of the medical event, the existence/likely existence of the medical condition, the onset/likely onset of the medical condition, or the decline/likely decline of the subject (who already has the medical condition) with respect to the medical condition. The signs may be considered as abnormalities, or abnormal changes, in the gait of an individual. For brevity, a system for predicting medical events and conditions that are reflected in gait may be referred to herein simply as a/the system.

Before turning to the figures, a brief, simplified summary/overview of such a system will be described. Such a system may include one or more data capture devices (e.g., imaging devices), a data analysis/output module, and a user interface. The data capture device(s) capture data pertaining to body motion of an individual (e.g., patient being monitored). The data analysis/output module analyses the captured data and, based on the analyzed data, generates output (e.g., predictions) as to the likelihood of the individual experiencing a fall, acquiring certain medical conditions, or the like. More specifically, the data analysis module extracts walking-pattern (i.e., gait) parameters from the captured body motion data and then, using, e.g., pattern recognition and machine learning algorithms trained with pertinent training data, predicts a risk or likelihood of certain medical events or conditions based on the extracted gait parameters, e.g., triggers an alert indicating such risk or likelihood if the analyzed data (e.g., extracted gait parameters) exceeds one or more thresholds. Different medical events and conditions may have different thresholds, and a given alert may indicate the type of medical event or condition. The prediction or alert, as well as data underlying the prediction or triggering the alert, may be transmitted to a user (e.g., clinician) via a user interface. The user may review this information received via the user interface and, based on the review, provide feedback to the system. The content of the feedback may be any or all of: verification data (confirming or disconfirming the validity of the prediction or alert) that may serve in effect as ongoing, additional training data for the system (which may improve system performance over time); an instruction to notify the patient of the prediction or alert, or to make a related notification; and an instruction to trigger medical intervention on behalf of the patient in view of the prediction or alert. The term "prediction" as used herein refers not only to predictions of future likelihoods of medical events or conditions but also to present likelihoods of such, i.e., potential diagnoses having a certain level of probability of being true. (For brevity, such potential diagnoses may be referred to herein simply as "diagnoses." Relatedly, it is to be understood that the systems, apparatuses, and methods disclosed herein are not intended to replace a physician or other diagnostician). Thus, the term "likelihood" refers not only to the probability of a future event occurring but also the probability that a current condition exists. While the term "patient" is used herein, it will be understood that the systems and methods disclosed herein are applicable to subjects who, strictly speaking, need not be patients, i.e., individuals under the care, observation or treatment of medical personnel, or individuals who are sick, disabled, etc. In fact, the systems and methods may be usefully applied to healthy or medically normal individuals, for the purpose of providing advance indication of potential medical events (e.g., falls) or conditions so as to permit proactive medical intervention in order to prevent or mitigate such events or conditions. To be sure, a system for predicting medical events and conditions that are reflected in gait may also be instantiated as any one or more of: (1) one or more data capture devices; (2) a data analysis/output module; and (3) a user interface. (The patient and user, as described herein, are not part of the disclosed systems for predicting medical events and conditions that are reflected in gait.)

The disclosed systems and methods for predicting medical events and conditions that are reflected in gait may be applicable to the following medical events and conditions: falls or similar events, osteoarthritis, Parkinson's disease, Dementia spectrum disorders, Alzheimer's disease, lower extremity orthopedic injuries, peripheral neuropathy, cardiovascular disease, and other medical events and conditions, e.g., such as may lead to accelerated functional decline.

Systems and methods for predicting medical events and conditions that are reflected in gait will now be described in greater detail with initial reference to FIGS. 1-3.

FIG. 1 is a block diagram illustrating such a system at a top level, according to some embodiments. FIG. 2 is a block diagram illustrating such a system in greater detail than that shown in FIG. 1, according to some embodiments. FIG. 3 is a block diagram illustrating a data capture subsystem of such a system, according to some embodiments.

With initial reference to FIG. 1, a system 100 for predicting medical events and conditions that are reflected in gait includes a data capture subsystem 110, a data analysis and output generation subsystem 120, and a user interface subsystem 130. The system 100 is designed for operation with a patient 140, i.e., for monitoring and evaluation of patient 140, with generation of output to a user, e.g., healthcare provider, for the purpose of mitigating potential future adverse medical effects on the patient 140. As FIG. 1 is a top level view, it does not necessarily cover all details and nuances of system 100. For example, FIG. 1 does not show all inputs to system 100. As another example, system 100 may include elements that are associated with particular subsystems but technically may not be deemed "part of" such particular subsystems; the rubrics used in FIG. 1 to identify the several subsystems do not take account of this distinction.

The data capture subsystem 110 may include one or more data capture devices. (The terminology "data capture" is understood to be equivalent to the terminology "data acquisition" or "data recording.") Where a plurality of data capture devices are used, they may be of the same or different kinds. The data capture subsystem 110 may include data capture device(s) of any of various types able to capture data pertaining to the gait of the patient 140 when the patient 140 is walking or performing similar locomotion or attempts thereat, e.g., kinematic data capture devices, kinetic data capture devices, electromyographic (EMG) data capture devices, and other gait data capture devices. In this context, kinematic data is data pertaining to position and/or motion of the patient 140 and/or of body parts of the patient 140; kinetic data is data pertaining to forces applied by the patient 140 or body parts of the patient 140 (e.g., foot pressure); and electromyographic (EMG) data is data pertaining to electrical activity of muscles of the patient 140. Further, kinematic data may be of any one or more of the following types: visual data, infrared data, radar data, and other image/kinematic data, any or all of which may be referred to herein generally as image data, kinematic data or the like. Exemplary kinematic data capture devices include cameras, sensors, or other devices for capturing image data, and the terms "imaging device" or "image data capture device" may be used to encompass any or all such devices. One of ordinary skill in the art will appreciate that in real world systems it is often feasible to substitute any of a variety of types of imaging devices for a given type of imaging device, and that in some cases different terms (e.g., "camera," "sensor," etc.) may be used to refer to the same type of imaging device. Cameras may include depth cameras or other types of cameras. Cameras may include those capable of recording still images, those capable of recording moving images (video), and those capable of recording both of these types of images. An exemplary camera for use according to some embodiments is the Microsoft™ Kinect camera. The Microsoft™ Kinect camera is an RGB-D camera. An RGB-D camera includes an RGB sensor and a depth sensor. Further information about the Microsoft™ Kinect camera can be found in "Easy-to-Use and Accurate Calibration of RGB-D Cameras from Spheres" (PSIVT 2013, LNCS 8333, pages 265-278, Springer-Verlag, 2014) by authors including two of the inventors of the instant application and "Evaluating the Accuracy of a Mobile Kinect-based Gait-Monitoring System for Fall Prediction" (PETRA '13, 2013) by two of the inventors of the instant application (which articles constitute Appendices A and B, respectively, to the provisional application to which the instant application claims priority) and, e.g., at www.microsoft.com/en-us/kinectforwindows. Another exemplary camera for use according to some embodiments is the ASUS™ XTion™ camera. Non-limiting examples of other cameras that may be used are given in the aforementioned articles. According to some embodiments, the data capture subsystem 110 may employ infrared (IR) cameras and reflective markers worn by the patient, such as exemplified by the Vicon™ motion capture system, which is described in the latter of the aforementioned articles. According to some embodiments, image capture devices may be configured to record video continuously. According to some embodiments, image capture devices may be configured to record video non-continuously, e.g., periodically, intermittently, or at the instruction of a user (e.g. clinician). According to some embodiments, image capture devices may be configured to record still (i.e., photographic) images, moving images (i.e., video), or both kinds of images, and on any continuous or non-continuous basis.

Figure 2:
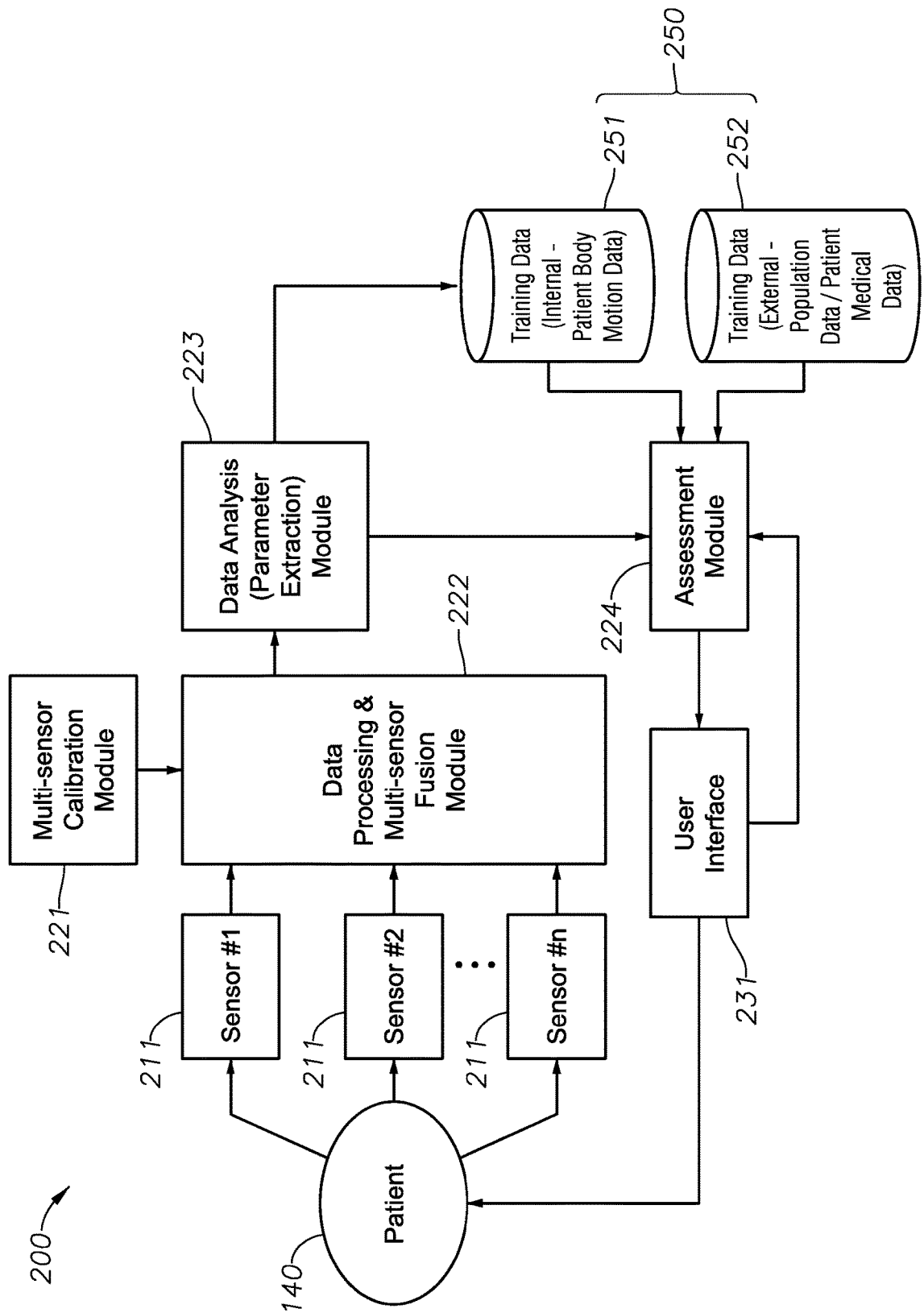
FIG. 2 is a block diagram illustrating, in greater detail than FIG. 1, a system for predicting medical events and conditions that are reflected in gait, according to some embodiments.

FIG. 2 illustrates a system 200, which is a more detailed version of system 100 shown in FIG. 1, according to some embodiments. As seen in FIG. 2, data capture subsystem 110 of FIG. 1 may include a plurality of sensors 211 (designated 1 to n); and data analysis and output generation subsystem 120 of FIG. 1 may include a multi-sensor calibration module 221, a data processing and multi-sensor fusion module 222, a data analysis (parameter extraction) module 223, and an assessment module 224. According to some embodiments, sensors 221 may be cameras or other imaging devices, and the calibration module 221 and fusion module 222 may be modified accordingly. With regard to data processing and multi-sensor fusion module 222, the data processing and the fusion may be performed independently of one another; in alternative embodiments, the system may include two separate and independent modules, one for data processing and one for multi-sensor fusion. The calibration module 221 may be deemed not to be a part of data analysis and output generation subsystem 120 of FIG. 1, in that the primary function of the calibration module is to calibrate the sensors prior to operation of the system. Training data 250 is inputted to assessment module 224. Some of training data 250 may be (based on data) generated by data analysis (parameter extraction) module 223 and accordingly may be designated as 'internal' to system 200 (internal training data 251), while some of the training data may be 'external' input (external training data 252) (discussed further below). FIG. 2 also shows a user interface device/module 231 but not in greater detail than the user interface subsystem 130 shown in FIG. 1; further detail of the user interface 130/231 is illustrated in, and discussed below with reference to, FIGS. 6A-6E and 9.

FIG. 3 illustrates an arrangement of a plurality of imaging devices 311, 312 that may be included in data capture subsystem 110, according to some embodiments. (For brevity, the following description of FIG. 3 refers to cameras, but imaging devices 311, 312 may be other imaging devices.) As seen in FIG. 3, data capture subsystem 110 may employ at least one mobile camera 311 and one or more (e.g., two, three or more) stationary (also referred to as "fixed") cameras 312. Mobile camera 311 may be a camera mounted on a robot (or other moving device) that is programmed to track patient 140 for the purpose of capturing kinematic data of patient 140 when patient 140 is moving. In this regard, tracking patient 140 may serve to keep patient 140 in the field of view of camera 311 even when patient moves 140. Tracking patient 140 may be performed, e.g., by following patient 140 at a (e.g., fixed or controlled) distance from patient 140. This motion of mobile camera 311 and patient 140 is indicated in FIG. 3 by the dashed arrowheads associated respectively with patient 140 and mobile camera 311. Mobile camera 311 may thus in effect be programmed to automatically track and record image data of patient 140. Inasmuch as mobile camera 311 is mounted on or otherwise incorporated in or incorporates a moving device, mobile camera 311 may effectively be deemed to move of its own accord (or, put in other words, to have an internal mechanism of motion). Mobile camera 311, and stationary cameras 312, may be non-wearable devices. According to some embodiments, stationary cameras 312 may be located in positions along a commonly traveled path of patient 140 such that one stationary camera 312 is located on the left side of patient 140 and one stationary camera 312 is located on the right side of patient 140, when patient 140 walks along the commonly traveled path. Other numbers and arrangements of cameras 311, 312 may be employed, as will be understood by those of ordinary skill in the art. For example, according to some embodiments, data capture subsystem 110 may have one or more stationary cameras 312 and no mobile cameras 311; and according to some embodiments, data capture subsystem 110 may have one or more mobile cameras 311 and no stationary cameras 312.

Prior to use of data capture subsystem 110 in an operational setting to capture data, the imaging devices (e.g., 211 or 311, 312) may be calibrated. Calibration may increase the accuracy of the captured data. Where data capture subsystem 110 includes a plurality of imaging devices (or more generally, data capture devices), not only may each imaging (data capture) device be calibrated with respect to itself, but also each imaging (data capture) device may be mutually calibrated with respect to every other imaging (data capture) device of data capture subsystem 110. This calibration is performed by calibration module 221 (FIG. 2). Once calibrated, the system (e.g., 100 or 200) may be used to carry out its purpose, without use of calibration module 221. Depending on the circumstances, after use of the system (e.g., 100 or 200) has commenced recalibration may be performed to recalibrate, or verify the calibration of, the imaging (data capture) devices. Such recalibration may improve the accuracy of the captured data. In view of the primary role of calibration module 221 as pertaining to setup of the system (e.g., 100 or 200), preliminary to use of the system to carry out its purpose, calibration module 221 may be deemed to be a part of the system 100 or 200 according to some embodiments and calibration module 221 may be deemed not to be a part of the system 100 or 200 according to some embodiments.

Specifically, calibration of the imaging devices (e.g., 211 or 311, 312) may be performed in the following manner. The following calibration method may be used for an RGB-D camera or for any arrangement of RGB and depth sensors. According to the method, a spherical object is moved in front of the camera for few seconds. An image processing (feature extraction) pipeline is used to automatically detect the moving spherical object and to discard spurious data such as noise and outliers, e.g., if present, a hand of a user holding the spherical object. A least-squares method is used to initialize (obtain initial estimates of) the camera calibration parameters (e.g., relative position and orientation, focal lengths, principal points, and lens distortion of the RGB and depth sensors). The initial estimates are used as inputs to a nonlinear minimization procedure to obtain refined estimates of all the calibration parameters of the RGB-D camera. This method is described in greater detail in the aforementioned article, "Easy-to-Use and Accurate Calibration of RGB-D Cameras from Spheres." While other calibration methods (examples of which are given in this article) may be used, this method provides advantages over prior art (e.g., checkerboard-based) methods. For example, this method is to a greater extent automated and hence can be performed by non-expert users (e.g., the patient, unassisted, in a home environment), whereas the prior art methods require expert user intervention. As another example, this method is more accurate and robust, e.g., reducing noise and rejecting spurious data. The advantages of the method are described in greater detail in the aforementioned article, "Easy-to-Use and Accurate Calibration of RGB-D Cameras from Spheres." It will also be understood by one of ordinary skill in the art that this method is not limited to spherical objects but may be used with any one or more three-dimensional objects, e.g., everyday objects commonly found in man-made, indoor environments such as a home, hospital, etc.

Certain problems arise in the attempt to capture individual body motion in an at-home, everyday, or normal living environment, as against in the controlled environment of a laboratory. First, the patient's body motion, or portions of it, may be blocked at times by the patient him/herself, or his/her body parts. This blockage may be referred to as self-body occlusion. By employing multiple imaging devices respectively at different positions and orientations (e.g., as discussed above, one each on the left and right side of a walking patient), the system may effectively overcome or mitigate this problem. In this regard, the system may also be enhanced to leverage body-motion models within machine learning algorithms (e.g., belief propagation) to infer the position of an occluded body part (e.g., a leg) by leveraging the position and/or motion of other, observable body parts (e.g., hip and torso). Another problem is that when the patient is in an area cluttered with multiple individuals, the imaging devices may not be able to distinguish the different individuals' motion. To solve or mitigate this problem, the system may incorporate a face recognition module, which uses face recognition algorithms to distinguish different individuals so that the system can associate captured body motion data with the correct individual. In this regard, a successful calibration may facilitate the accurate detection of the patient's body motion, by superposition of the detected face in a color (or RGB) imaging device on the detected body-pose parameters.

After the data is captured by the data capture device(s) (e.g., 211 or 311, 312, or kinetic, EMG or other data capture devices), the data processing component of data processing and multi-sensor fusion module 222 may employ signal processing methods to automatically suppress noise and artifacts in the captured data. Such methods are known to one of ordinary skill in the art and may include the use of, e.g., Finite Impulse Response filters or Kalman filters.

Where data capture subsystem 110 includes a plurality of imaging devices (or more generally, data capture devices), the data captured from the several devices is fused so as to yield a coherent set of image (or force, EMG, etc.) data based on the collective data from the several devices. This data fusion is performed by the multi-sensor fusion component of the data processing and multi-sensor fusion module 222, in a manner that will be understood by one of ordinary skill in the art. For example, one possible approach would be to employ Bayesian data-fusion strategies that fuse body-motion observed from multiple imaging devices according to their respective uncertainties, so that measurements from devices having a greater degree of uncertainty have less impact on the result of the fusion.

After the data from the multiple data capture devices are fused, gait parameters are extracted from the fused data, e.g., by the data analysis (parameter extraction) module 223 using signal processing methods within the purview of those of ordinary skill in the art (e.g., Kalman filtering or direct computation of center of mass). As will be understood by one of skill in the art, there are a variety of parameters that characterize gait that may be extracted for the purpose of the system. These parameters include, for example: stride length, stride duration (gait cycle), center of mass motion (position, velocity), anteroposterior angle, mediolateral angle, knee angles, double stance time (double support interval), step asymmetry, gait asymmetry, gait speed, gait freezing, and other parameters. (The parameters 'anteposterior angle' and 'mediolateral angle' are explained in the aforementioned article, "Evaluating the Accuracy of a Mobile Kinect-based Gait-Monitoring System for Fall Prediction.") One or more of these parameters may be extracted and used by the system to generate output. According to some embodiments, the system may extract the position and/or velocity of the anthropometric center of mass (COM) and use only these parameters to generate output. According to some embodiments, the system may extract the position and/or velocity of the anthropometric COM and, optionally, the anteroposterior and mediolateral angles, and optionally, the knee angles, and use only these parameters to generate output. Use of these few parameters serves the purpose of data reduction while retaining accuracy. According to some embodiments, the system may extract any one or more of the aforementioned or other gait parameters and use that/those parameter(s) to generate output.

After completion of the data analysis (extraction of the gait parameters), the analyzed patient data (reflecting the current values of the extracted gait parameters, which may also be referred to as current patient data) is inputted to the assessment module 224.

Prior to use of the system (e.g., 100 or 200) in an operational setting to generate output, training data 250 is inputted to the assessment module. The training data serves generally as a baseline against which the analyzed (current) patient data received from the data analysis (parameter extraction) module 223 is compared. The training data 250 may include population data, that is, data from individuals other than the patient, and/or historical patient data, that is, previously acquired data of the particular patient being monitored by the system.

The population training data may include "normal" data and may also include "abnormal" data. The normal data may be data that is comparable in type to the current patient data and that represents normal individuals, i.e., individuals the values of whose gait parameters fall within the normal range. Similarly, the abnormal data may be data that is comparable in type to the current patient data and that represents abnormal individuals, i.e., individuals the values of whose gait parameters fall outside of the normal range. The abnormal data may include multiple data sets representing different types of abnormal conditions, respectively, e.g., data of individuals prone to fall, data of individuals who have or are expected to acquire a particular neurodegenerative condition (e.g., Parkinson's disease) or other adverse medical condition (e.g., an adverse cardiovascular condition), etc. Further, for a given patient being monitored by the system, the population data used may be data from populations that are the same as or comparable to the patient in terms of gender, age, or other characteristics. For example, for a female patient of age 75, population data of female individuals in the age range of 65 to 85 may be used. As another example, for a patient having or expected to acquire Parkinson's disease, the abnormal population data may include data from individuals having Parkinson's disease.

The historical patient data may include previously acquired gait data of the patient. This may include normal and abnormal data of the patient (to the extent available) and will serve as a baseline for comparing current patient data. The historical patient data may also include what may be referred to as historical patient metadata. Historical patient metadata is not gait data but data pertaining to external conditions that bear on gait, e.g., the patient's medical data. An example of this is as follows. A patient's gait may be affected, e.g., by a new drug prescription that the patient recently started taking, by a reduction in the patient's visual acuity and/or field, by hip surgery that the patient recently underwent, etc. Accordingly, the patient's medical data indicative of such medical event/condition may be inputted as training (meta)data so that the effect of such medical event/condition may be taken account of in evaluating the patient's current gait data. In this case, of course, the training (meta)data does not serve as a baseline against which the patient's current data is compared but rather serves as a correction factor compensating for a known condition that affects gait.

With regard to the above discussion of training data 250, the previously acquired gait data of the patient may be referred to as internal data 251 (i.e., data generated by the system), while the population data and historical patient metadata may be referred to as external data 252.

The examples of training data 250 given are not to be taken as limiting, and any one or more kinds of data may be used for any type of patient or particular patient. Medicine being partly an art and not entirely a science, the particular facts or circumstances of a particular patient may warrant any of such various types, or combinations of types, of data being used as training data 250.

The assessment module 224 may use, e.g., artificial intelligence techniques and machine learning strategies within the purview of those of ordinary skill in the art (e.g., Nearest-Neighbor voting, Support Vector Machine, Neural Networks, etc.), to generate an assessment of the patient based on an evaluation of the patient's current data in light of the training data. Such assessment may indicate, e.g., (1) a diagnosis of a particular medical condition, e.g., neurodegenerative disease (or an assessment of the likelihood that the patient has such particular medical condition), or (2) a risk assessment (or likelihood prediction) of the patient's risk of falling (or of experiencing a similar medical event), of the patient's acquiring a particular medical condition, of the patient's declining to a certain extent with respect to an existing medical condition, etc. The assessment may be, on the one hand, general, or high level (e.g., indicating merely that a patient is "at risk" or "normal"), or, on the other hand, lower level. Lower level assessments may, as suggested above, indicate a type of risk, i.e., the type of medical event/condition for which the patient is at risk (e.g., "At risk—fall," "At risk—arthritis," etc.). In this regard, it is noted that different particular kinds of gait abnormality (e.g., abnormalities in different particular gait parameters) may be associated with different particular medical events/conditions, respectively, e.g., an increase in double stance time may be predictive/indicative of Alzheimer's disease in older adults, a change in gait speed or gait asymmetry may be predictive/indicative of osteoarthritis, etc. Lower level assessments may also indicate a level of risk (e.g., "At risk—high," "At risk—moderate," or "At risk—low"; or "At risk—x," where x is an integer between 1 and 10, with 10 indicating the highest level of risk and 1 indicating the lowest level; etc.). The assessment may also be a relative assessment, i.e., indicating the change (in risk or likelihood) relative to a previous assessment of the patient.

The assessment module 224 may generate the assessment, e.g., based on whether the analyzed data (e.g., the value(s) of one or more given gait parameters (or the magnitude(s) of the motion of one or more given body parts)) exceeds one or more thresholds. (For the sake of brevity, the description herein will assume that assessments are based on exceeding a single threshold rather than multiple thresholds.) The threshold may be determined by the range of values of the given gait parameter (or the range of magnitudes of the motion of the given body part) exhibited by (a population sample of) normal individuals. The normal individuals may have been selected based on the fact that they share certain medically relevant characteristics with the patient being monitored, e.g., age (range), gender, medical history (history of medical conditions, current medication, etc.), etc. Alternatively, or in addition, the threshold may be determined by the range of values of the given gait parameter (or the range of magnitudes of the motion of the given body part) heretofore exhibited by the patient being monitored. Finally, the threshold may be determined also by (taking account of) the medical history or other pertinent facts of the patient being monitored. All of the data mentioned here as the basis for determining the threshold will have been inputted to the assessment module 224 as training data 250 prior to the assessment module's generation of the assessment. However, additional such training data 250 may continually be inputted into the assessment module 224 on an ongoing basis, as new training data 250 is acquired. Where a patient is being monitored on an ongoing basis, new training data 250 consisting of historical gait/body motion data of the patient would be acquired on an ongoing basis and inputted into the assessment module 224 on an ongoing basis. Training data 250 consisting of medical history/facts of the patient would be acquired only as pertinent such events occur, and so would generally be inputted into the assessment module 224 less frequently than training data 250 consisting of historical gait/body motion data of the patient. Also, training data 250 consisting of gait/body motion data of a normal population sample would generally be acquired, and hence inputted into the assessment module 224, less frequently than training data 250 consisting of historical gait/body motion data of the patient.

If the analyzed data of the patient (e.g., the value of a given gait parameter of the patient (or the magnitude of the motion of a given body part of the patient)) exceeds a threshold, an algorithm in the assessment module 224 may trigger an alert to indicate that an 'abnormal gait event' has occurred. The alert may cause the system to insert an annotation in the captured (e.g., image) data at the time of the alert, e.g., so as to mark off, as a discrete segment of data (also referred to as a discrete 'event'), a short duration of the captured (e.g., image) data, as video recording, including a short period of time on either side of the time at which the threshold was exceeded. This discrete event may be referred to as an abnormal gait event in that during this event the patient manifested an abnormal gait, or abnormal change in gait, as reflected by the fact that the threshold was exceeded. (Thus, an abnormal gait event may be thought of as a period of time during which the patient exhibited abnormal gait.) According to some embodiments, the duration of the short period of time on either side of the time at which the threshold was exceeded may be set so as to generally include (or aim to include) some amount of time during which the patient's gait did not manifest the abnormality. The provision to the user of video (or other captured data) of both abnormal gait and normal gait will permit the user to evaluate the abnormal gait against a baseline of normal gait of the patient. According to some embodiments, the system may provide the user with a separate video recording (or other captured data) of the patient exhibiting normal gait ('normal gait event'), in which case it would not be necessary for the abnormal gait event to also include some amount of time during which the patient's gait did not manifest the abnormality.

In addition to generating an assessment (e.g., risk assessment or diagnosis) as described above, the assessment module 224 may output the discrete abnormal and normal gait events. This output may include, e.g., a listing of the events and video recordings (or, more generally, data recordings) of the events. The listing may identify the events by any one or more of various characteristics, e.g., date and time of occurrence (see discussion of FIG. 6B below), classification as normal or abnormal (see discussion of FIG. 6B below), classification as to abnormal event type (i.e., identification of particular medical event/condition for which a risk/likelihood is indicated by the given abnormal event) (see discussion of FIG. 6B below), classification as to level of risk/degree of likelihood (see discussion of FIG. 6B below), magnitude of deviation from (extent of body motion beyond that of) normal gait (i.e., extent to which value of gait parameter/magnitude of body motion exceeds the threshold) (see discussion of FIG. 6E below), classification as to which particular joints'/body parts' motion exceeded the threshold (see discussion of FIG. 6D below), etc. A video (or more generally, data) recording of an event may present the event as it happened in real time with some degree of similitude, in terms of human perception, to the event as it occurred in real life (see discussion of FIG. 6C below).

The system may save the listing and recordings of the events for later review by a user, e.g., clinician. The user may select any one or more of the events from the list to see its characteristics and to view its video recording (see discussion of FIG. 6B below). In this way, the user may easily access and review abnormal gait events of the patient without having to watch excessively lengthy video recording of the patient or to wade through excessive amounts of gait/body motion data of the patient. The user may view a recording for purposes of evaluation, verification (described below), obtaining further qualitative understanding, etc., of the abnormal gait event. In this regard, whereas the above-described assessment (e.g., risk assessment or diagnosis) generated by the assessment module 224 may be understood as a (medical) conclusion, the above-described discrete events (the listing/characteristics and video recordings thereof) may be understood as evidence in support of the assessment/conclusion.

Upon viewing the recording the clinician may provide feedback to the system, and the system may receive the feedback. The feedback may be, e.g., one of three types: verification feedback provided as input to the assessment module 224; notification to the patient; and feedback triggering medical intervention.

As for verification feedback, the clinician may provide confirmation or disconfirmation of the abnormal gait event. Confirmation/disconfirmation would occur where the clinician by viewing the recording confirms/disconfirms that the event was truly/was not an abnormal gait event. For example, the recording may show that the apparently abnormal gait event was in fact due to a non-medical cause, e.g., the patient's gait changed because the patient slowed down to look at a handheld cell phone, or because the patient reached down to pick up something from the ground. In this case, the clinician would disconfirm the event. Such disconfirmation provided (fed back) to the assessment module may be used as metadata, as a correction factor, whereby the assessment module can improve its ability to avoid identifying such false positives as abnormal gait events. The provision of verification feedback thus amounts to a feedback loop (as indicated by the arrow going from the user interface 130, 231 to the assessment module 224 of the data analysis/output generation subsystem 120 in FIGS. 1 and 2) in the machine learning aspect of the system 100, 200 whereby the system 100, 200 can improve its performance.

As for notification to the patient 140, the clinician may provide input to the system 100, 200 instructing the system 100, 200 to notify the patient 140. Such notification may be transmitted to the patient 140 by any communication means, e.g., wireless or wired (discussed below with reference to FIGS. 8 and 9). Such notification may, e.g., inform the patient 140 of an abnormal gait event, instruct the patient 140 to take precautionary measures, to take medication, or to contact a physician, etc.

As for feedback triggering medical intervention, the clinician may provide input to the system 100, 200 instructing the system 100, 200 to add a notation to the patient's medical record, to send a notification to the patient's doctor, etc. Such notification may be transmitted by any communication means, e.g., wireless or wired (discussed below with reference to FIGS. 8 and 9).

As will be understood from the description herein, the several subsystems (e.g., shown in FIG. 1), and various elements of any given subsystem (e.g., shown in FIG. 2) may (but need not) be physically separate from one another. In such case, data may be transferred between these subsystems and elements by means of any suitable wired or wireless communication platform, e.g., telephone (wired or wireless), pager, the Internet, etc., as will be understood by one of ordinary skill in the art and as further described below with reference to FIGS. 8 and 9. Also, data may or may not be transmitted and/or processed in real time.

As discussed above, the system 100, 200 may receive, on an ongoing basis, additional training data 250 (e.g., gait data of the patient, which is continually being acquired) as well as feedback from the clinician serving as corrective training (meta)data. Using these two types of data, the system 100, 200 may improve its performance. First, the assessment module 224 may better assess the analyzed data it receives. More fundamentally, the system 100, 200 may learn which gait parameters yield better predictions for a particular patient 140 being monitored, or which gait parameters yield better predictions of a particular medical event/condition being monitored for. The system 100, 200 may then self-select particular gait parameters for extraction and making assessments based thereon. This self-learning by the system 100, 200 may be effected by use of statistical analytical methods such as principal component analysis (PCA), as will be understood by those of ordinary skill in the art.

Figure 5:
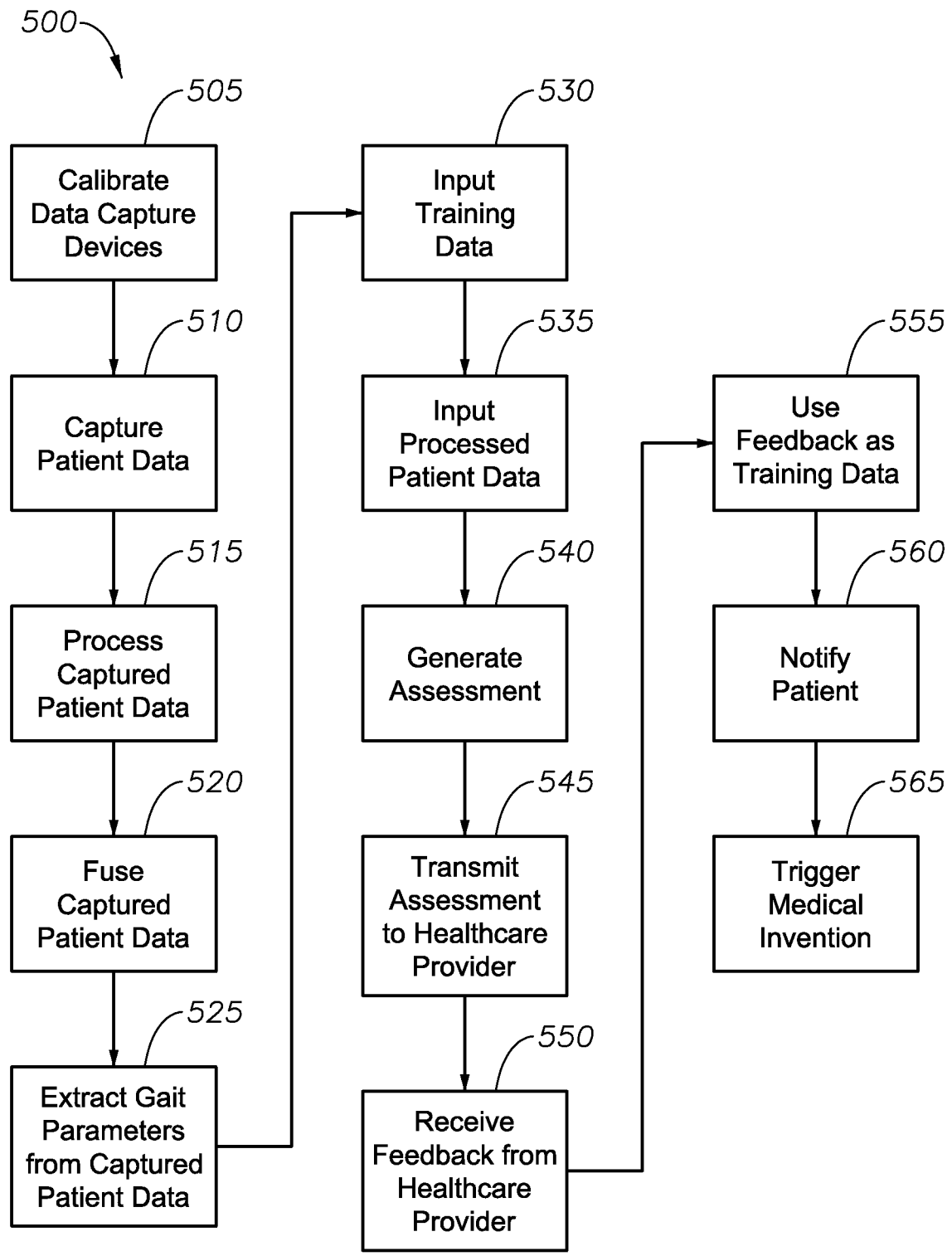
FIG. 5 is a flow chart illustrating, in greater detail than FIG. 4, a method for predicting medical events and conditions that are reflected in gait, according to some embodiments.

FIGS. 4 and 5 are flow charts illustrating methods of operation of system 100, 200, i.e., methods of predicting medical events and conditions reflected in gait. FIG. 4 illustrates a method 400 at a top level, while FIG. 5 illustrates a method 500 at a more detailed level. It will be understood that the descriptions of FIGS. 4 and 5 provide only brief accounts of steps and processes that are described in greater detail elsewhere in this disclosure.

As seen in FIG. 4, at step 410, data of a patient being monitored is captured by one or more data capture devices (e.g., 110, 211, 311, 312). At step 425, the captured data is analyzed by a data analysis module (e.g., 120, 223). At step 440, output, e.g., an assessment and supporting evidence, is generated by an assessment module (224), based on the analyzed data. The assessment may be a medical assessment as to risk of falling, neurodegenerative condition, or the like. The evidence supporting the assessment may be, e.g., a video recording of an abnormal gait event, or other presentation of the analyzed data, etc. as discussed elsewhere herein, for example with reference to FIGS. 6B-6E. At step 445, a healthcare provider is informed of the output (e.g., assessment and supporting evidence), via a user interface (e.g., 130, 231). At step 450, the user interface (e.g., 130, 231) receives feedback from the healthcare provider in response to the output. The feedback may be in the form of, e.g., verification feedback, notification to the patient, or triggering of medical intervention, as described above.

As seen in FIG. 5, at step 505, a plurality of data capture devices (e.g., 211, 311, 312) are calibrated. Each device is calibrated internally, and the several devices are mutually calibrated with one another. According to some embodiments, a portion of the calibration may be performed by a human actor, and step 505 may encompass only the portion of the calibration performed by machine. At step 510, data of the patient (140) being monitored is captured by the data capture devices. At step 515, the captured patient data is processed. The processing may include suppression of noise and/or artifacts. At step 520, the captured patient data from the multiple data capture devices is fused to form a single set of coherent, collective data from the multiple devices. At step 525, gait parameters are extracted from the fused data.

At step 530, training data (250) is inputted into an assessment module (224) of a data analysis/output generation subsystem (120). At step 535, the processed patient data is inputted into the assessment module (224). At step 540, output (e.g., an assessment and supporting evidence) is generated by the assessment module (224). At step 545, the output is transmitted to a user (e.g., healthcare provider). At step 550, the assessment module (224) receives feedback from the user (e.g., healthcare provider). At step 555 the feedback is used as additional training (meta)data (corrective data) by the system (e.g., assessment module 224). At step 560, the system notifies the patient (140), pursuant to the feedback. At step 565, the system triggers medical intervention on behalf of the patient (140), pursuant to the feedback.

The method 500 shown in FIG. 5 may be appropriately modified if only one rather than a plurality of data capture devices is used. For example, in this case step 505 could be modified (as there is no need for mutual calibration of one data capture device with another) and step 520 (data fusion) would be eliminated.

As will be understood by one of ordinary skill in the art, many other variations of the method 500 shown in FIG. 5 are also possible. For example, step 530 (input training data 250) may occur at an earlier stage in method 500. As another example, any or all of step 550 and subsequent steps (receipt and use of feedback) could be eliminated.

FIGS. 6A-6E illustrate exemplary screenshots of a user interface (e.g., 130, 231) for a system (e.g., 100, 200) and method (e.g., 400, 500) for predicting medical events and conditions that are reflected in gait, according to some embodiments. The user interface (e.g., 130, 231) is for interfacing with a user, who may be, e.g., a healthcare provider, such as a clinician, therapist, doctor, hospital, nurse, home health aide, etc. According to some embodiments or variant applications, the user may be the patient 140 being monitored. As described elsewhere herein in greater detail, the user interface 130, 231 may serve or facilitate serving the function of notifying the user of potential medical issues of the patient 140 being monitored so as to promote early medical intervention for the purpose of mitigating those medical issues. As described elsewhere herein, the user interface 130, 231 may also serve or facilitate serving other functions (e.g., the provision of training (meta)data on an ongoing basis for the purpose of improving system performance). The user interface 130, 231 may be implemented on an electronic device (e.g., mobile phone, tablet, laptop or desktop computer, etc.) by a software application, as described further below with reference to FIG. 9. As the screenshots shown in FIGS. 6A-6E are merely exemplary, innumerable variations on them may be implemented and are contemplated.

Any ones of the screenshots shown in FIGS. 6A-6E may be displayed as separate screenshots or may be combined as portions of the same screenshot. For the sake of convenience, in the description of FIGS. 6A-6E below it is generally assumed that these figures represent separate screenshots, but in any event the description below should not be taken as contradicting, superseding or otherwise limiting the previous sentence.

The description of the screenshots of FIGS. 6A-6E below may to some extent present information pertaining to the operation of disclosed systems (e.g., 100, 200) or methods (e.g., 400, 500) that has already been described above. However, the below description presents this information from the perspective of the user using the user interface 130, 231. In this regard, it will be noted that while the instant description refers to "output" (pertaining to a likelihood of the patient 140 experiencing a medical event or medical condition) generated by the data analysis/outcome generation module 120 or assessment module 224 and outputted to the user interface 130, 231, from the point of view of the user/user interface 130, 231 this "output" is actually input received by the user interface 130, 231. Accordingly as a perspective-neutral term, the term "information" may be used to refer to this output of the data analysis/outcome generation module 120 or assessment module 224, which constitutes input for the user interface 130, 231. This "information" is displayed or otherwise presented to the user. In response to this information" the user may provide feedback (input feedback into the user interface 130, 231), as discussed herein.

FIG. 6A illustrates a button 605 labeled "Record Data." This button 605 may appear as part of another screen. The user may touch (press, etc.) the "Record Data" button 605 to manually start monitoring a patient 140. For example, the "Record Data" button 605 may activate the data capture devices (e.g., 211, 311, 312) or, in alternative embodiments, the data capture devices may be operating continually but not necessarily recording or storing the captured data continually, and the "Record Data" button 605 may activate recording or storage of the captured data. Once touched (pressed, etc.), the displayed "Record Data" button 605 may change so as to display a "Stop Recording" button (not shown), and touching (pressing, etc.) the "Stop Recording" button may cause the data capture devices to be turned off, or the recording or storing of the captured data to be terminated. As will be understood by one of ordinary skill in the art, alternative arrangements, e.g., alternative on-screen displays, and alternative modes of operating such function of data recording (including automatic and pre-programmed modes), may be employed. For example, in alternative embodiments, the system may be pre-programmed, e.g., by a user, to automatically capture and record/store data at specified times for specified durations of time. In further alternative embodiments, data may be captured and recorded/stored continually (e.g., automatically). In such embodiments having automatic and/or pre-programmed modes of capturing and recording/storing data, the "Record Data" button 605 may optionally be eliminated from the user interface 130, 231.

Figure 6C:
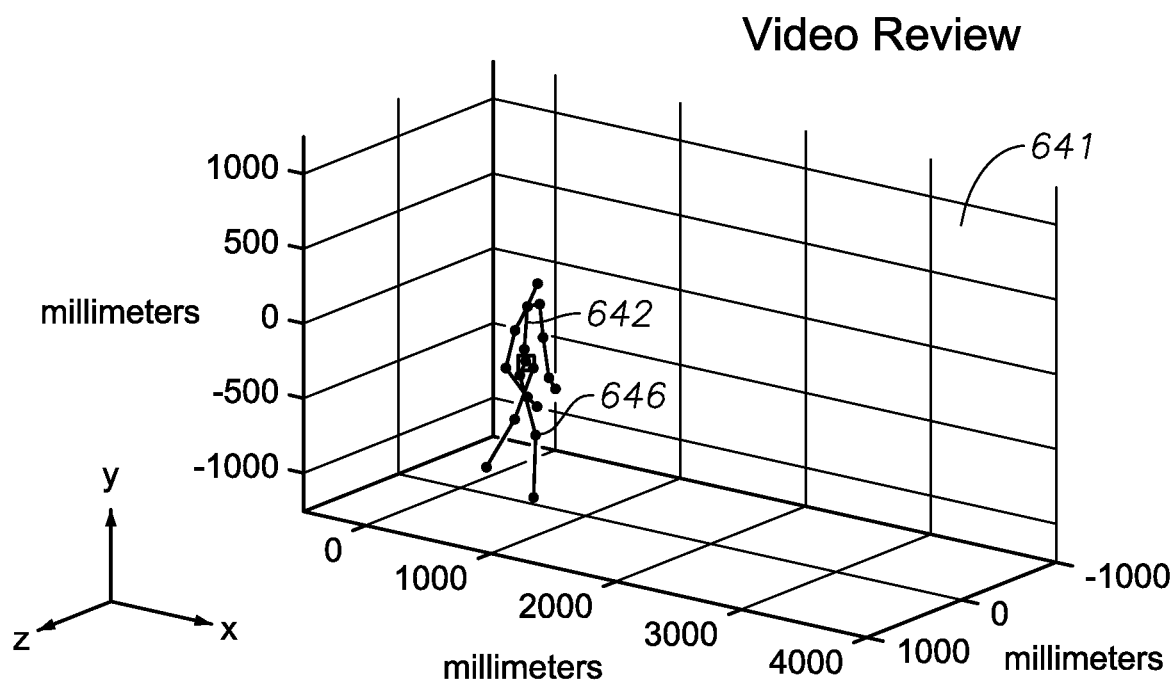

FIG. 6B illustrates a screenshot entitled "Recordings and Status." This screenshot illustrates a list 610 of recorded events, each event indicated, e.g., by an index number 611 (e.g., 1, 2, . . . ) and a filename 612 (e.g., "walking_experiment_1.txt"). The events may have been recorded over an extended period of time. Such an extended period of time may be a period of time that is longer than would be comfortable or convenient for a user (e.g., reviewing clinician) to spend constantly watching or reviewing a recording (e.g., video) of a patient (140) being monitored, e.g., a day or another period of time. In contrast, an individual event (e.g., the event recorded in the file named "walking_experiment_1.txt") may have a duration that is medically warranted (e.g., the time period of and around a fall by the patient, or a time period during which the patient's gait changed significantly) and that generally would not exceed a reasonable attention span expected of a reviewing clinician. Accordingly, the user may select (e.g., highlight and click on) any one of the events listed in the list 610 in order to view a recording of the individual event, described further below with reference to FIG. 6C.

While list 610 of recorded events in FIG. 6B lists only two events, in practice it is expected that list 610 may include numerous events, which have been (triggered and) recorded over the course of the extended period of time, e.g., day. Additional settings may be provided to give the user the option to retain or delete individual events after the end of each extended period of time, e.g., after the end of each day. This option may be able to be exercised in a manual or an automatic manner. The software application may be configured to permit being preprogrammed in this regard.

With continued reference to FIG. 6B, an event would generally correspond to a period of time during which the patient manifested an abnormal gait or an abnormal change in gait (including e.g., a change from a normal gait to an abnormal gait). An abnormal gait or change is one that indicates a risk (or likelihood), or a heightened risk (or likelihood), that the patient will experience an adverse medical event (e.g., a fall) or has/will acquire/will decline with respect to an adverse medical condition (e.g., neurodegenerative or other condition). Optionally, the software application may also include an event that corresponds to a period of time during which the patient manifested a normal gait or normal change in gait. Such normal event may serve as a baseline for comparison (performed by a reviewing clinician using the application) with abnormal events. The illustrated category labeled "Status" indicates the status 613 of an event, e.g., whether a given event is an abnormal ("at risk") event or a "normal" event. The illustrated category labeled "Permission" indicates by means of numerical symbols 614 whether the patient who has been recorded has given permission to the user (e.g., clinician) to view an actual video of the given event. As for the numerical symbols 614, a "0" may be used to indicate that permission has not been given, while a "1" (not shown) may be used to indicate that permission has been given. Where permission is given, the user may view an actual video of the given event; where permission is withheld, the user may view a filtered (or 'redacted') version of the video, which shows the three-dimensional body motion of the patient by means of a schematic version of the moving patient, resembling a stick or skeletal figure, as illustrated in FIG. 6C (described further below). The patient 140 may give/withhold permission by entering an input indicating that permission is given/withheld (for this purpose the patient 140 may be provided with a patient user interface (not shown), which may be an element distinct from the user interface 130, 231 discussed throughout this disclosure). Alternatively, the patient 140 may give/withhold permission, e.g., by informing the clinician, with the clinician then manually inputting this information into the application. This giving/withholding of permission may be performed, e.g., at or shortly after the occurrence of the event (the patient 140 being notified of the event by a notification mechanism), at or prior to the outset of the monitoring operation, or at any time. Other variations of the procedure for giving/withholding permission may be implemented, as will be understood by one of ordinary skill in the art.

FIG. 6C illustrates a screenshot entitled "Video Review." This is a screenshot for illustrating a video recording of a selected event (from the list 610 of events, FIG. 6B), either an actual video recording or a filtered ('redacted') video recording, depending on whether permission to view an actual video recording was given by the patient 140, as discussed above. As here illustrated, FIG. 6C shows a filtered video recording of the event. In the filtered video recording, the patient is represented schematically 642, showing key joints 646 (discussed in further detail with reference to FIG. 6D below) and the motion of body parts as well as of the patient as a whole (i.e., walking) Further, the video recording is set upon a three-dimensional Cartesian coordinate system 641 defined by x, y and z axes, with respect to which movement (distance moved) of the patient/patient's body parts may be measured. In FIG. 6C, the units on the x, y, and z axes are millimeters. In FIG. 6C, the schematic patient 642 is shown walking in the positive x direction (rightward in the figure). Given this orientation of the patient 642, if the patient 642 were to move sideways, the patient 642 would be moving in the z direction. The y direction represents upward/downward movement for the patient 642. One of the purposes of the permission feature and the filtered (redacted) video feature described above is to give the patient 140 the option of preserving a measure of privacy by withholding permission and thereby preventing the user from viewing the actual video recording. With this in mind, the term "redacted" is used to convey the function of the filtering of the video recording. Accordingly, it will be understood that the "filtering" of the video recording is distinct from the "filtering" of the captured data for the purpose of suppression of noise/artifacts described above in the context of data processing (see the discussion of the data processing and multi-sensor fusion module 222 of FIG. 2 and the discussion of step 515 ("process captured patient data") of FIG. 5).

Again, if the user had been given permission to view an actual video recording of a given event, then selecting the given event in the screenshot of FIG. 6B would result in the user seeing an actual video recording instead of a filtered video recording such as shown here in FIG. 6C.

In any event, the video review, whether actual or filtered, permits the user (e.g., clinician) to review the events and, based on the review, to provide feedback to the system (e.g., 100, 200). As discussed, the feedback may be, e.g., one of three types: verification feedback provided as input to the assessment module 224; notification to the patient 140; and feedback triggering medical intervention. As for verification feedback, the screenshot of FIG. 6B may further display a "Confirm" category (not shown) to the right of the "Permission" category. In the "Confirm" category, e.g., a "yes" button and a "no" button (not shown) may be displayed to the right of each listed event. The user may confirm the event by pressing the yes "button" or disconfirm the event by pressing the "no" button. For the sake of this discussion, suppose the event is an abnormal (rather than a normal) event. The clinician would confirm the event if upon viewing the video recording of the event the clinician determined that the event was properly triggered, i.e., the event was correctly identified as an abnormal event. The clinician would disconfirm the event if upon viewing the video recording of the event the clinician determined that the event was improperly triggered, i.e., the event was incorrectly identified as an abnormal event. For example, if the video recording showed that the patient's gait changed because the patient slowed down to look at a handheld cell phone, or because the patient reached down to pick up something from the ground, the clinician may determine that the event was improperly triggered, i.e., the event was incorrectly identified as an abnormal event. It is understood that in some, most or all cases, the clinician would be able, by virtue of merely watching the video recording, to make the determination as to whether the event was properly triggered or not, i.e., whether the event was truly an abnormal event. Again, the actual arrangement (e.g., display, mode of operation) for confirming/disconfirming events may vary from the implementation described here.

As for notification to patient and feedback triggering medical intervention, the user interface (130, 231) of the software application could be configured to provide a way for the user to input this kind of feedback, as will be appreciated by one of ordinary skill in the art.

Drawing on the discussions of FIGS. 6B and 6C, speaking in terms of the elements of system 100, it may be said that data capture subsystem 110 is configured to produce video recording of patient 140 covering an extended period of time, data analysis and outcome generation subsystem 120 is configured to identify and output discrete segments of the video recording corresponding to respective abnormal gait events of patient 140, each segment covering a short period of time, and the user interface subsystem 130 is configured to permit the user to selectively access the discrete segments of the video recording.

FIG. 6D illustrates a screenshot entitled "Status." This screenshot shows an image of a human figure that is used to represent the patient being monitored. This image may be referred to as patient image 644. Patient image 644 may be displayed as part of another screenshot or by itself. In FIG. 6D, the illustrated solid circles on the human figure indicate twenty key joints 646 of the patient: head, neck, right shoulder, right elbow, right wrist, right hand (at fingers), left shoulder, left elbow, left wrist, left hand (at fingers), mid-spine, base of spine, right hip, left hip, right knee, left knee, right ankle, left ankle, right foot (at toes), left foot (at toes). (Lines 647 connecting joints 646 represent skeletal connections between joints 646, but any given line 647 does not necessarily indicate whether the two joints 646 spanned by the line given 637 are connected by a single bone or by multiple bones.) Although not seen in FIG. 6D, this screenshot may be modified to illustrate or otherwise indicate the position of each of the twenty key joints 646, e.g., in terms of x, y, and z coordinates in a Cartesian coordinate system. By "key joint" is meant that motion of limbs (or body parts) connected to these joints may be a significant indicator of a (heightened) risk that the patient 140 will experience an adverse medical event (e.g., a fall) or has/will acquire/will decline with respect to an adverse medical condition (e.g., neurodegenerative or other condition). The system may track the positions of all or a subset of these twenty joints 646. In some embodiments, different sets of joints may be used, and such sets may include one or more joints not listed here. It will be understood that gait, and hence the monitoring and analysis of gait, involves not merely the motion of the lower portion of the body (e.g., feet, legs, hips) but also the motion of the upper portion of the body (e.g., arms, back, head).

Selecting a particular event from the list 610 shown in FIG. 6B causes a circle 643 (as illustrated in FIG. 6D) to appear on the patient image 644 of FIG. 6D. Specifically, the circle 643 is made to appear in such position as to surround the particular ones of the joints 646 (or the particular body parts) the movement of which triggered this particular event (again, for the purpose of this discussion it is assumed that the event is an abnormal event rather than a normal event). The identification of the particular joints (or body parts) the movement of which triggered the particular event is of interest because, e.g., different pathologies may be associated with abnormal movement of different parts of the body. Thus, the fact that a particular body part is circled 643 may indicate that the patient 140 has, or is at risk for, a particular medical condition, etc.

In some cases, the fact that a particular body part is circled 643 may reflect a certain happening in the patient's (e.g., recent) medical history, e.g., circling of the hip may reflect that the patient 140 recently had hip surgery, circling of a particular body part may reflect that the patient 140 recently started taking a certain medication, etc. In such cases, where the cause of the gait abnormality is thus known (based, e.g., on medical history), and if the gait abnormality does not indicate a risk that needs to be kept in check, the user (e.g., clinician) may raise the threshold for triggering abnormal events involving the particular body part in question. For example, if the patient manifests abnormal hip motion due to a recent hip surgery and this abnormal hip motion does not indicate a risk (e.g., a risk of falling or a risk of another medical condition) that needs to be kept in check, the clinician may raise the threshold for triggering abnormal events involving the motion of the hip. Thus, if the threshold for triggering an abnormal event involving the hip had been set at x mm (i.e., an abnormal event would be triggered if the hip moved a distance of x mm), the clinician might raise the threshold to (x+n) mm. This is a hypothetical and simplified example. In practice, a threshold may be more complex than simply movement by a certain distance. For example, a threshold based on movement may involve distance in more than one direction (e.g., x, y, and/or z directions in FIG. 6C); moreover, a threshold may be based on more than one parameter, e.g., position and speed, or other combinations of parameters, which parameters may be related to each other to greater or lesser degrees and may pertain to different body parts, etc.

The clinician may also adjust the threshold based on factors other than the patient's medical history. For example, the clinician may raise the threshold based on the previously acquired gait data of the patient 140. To further specify the example, where the patient's gait deviates from that of the normal population, the clinician may direct the system to provide output of subsequent abnormal gait events only where the patient's deviation exceeds the magnitude of the previously recorded deviations of the patient 140 (e.g., because otherwise there would be an overwhelming amount of output for the clinician to review), assuming the clinician deems such reduced level of monitoring not to pose an undue medical risk to the patient 140.

Figure 6E:
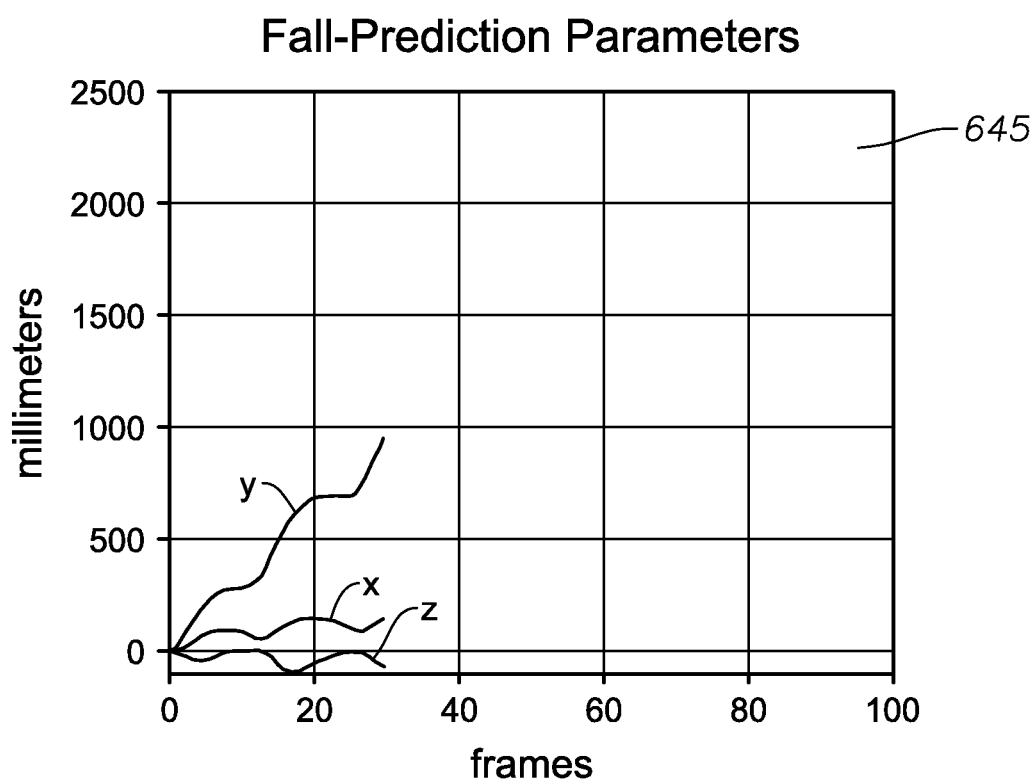

FIG. 6E illustrates a screenshot entitled "Fall-Prediction Parameters." The screenshot shows a two dimensional Cartesian coordinate system 645 in which the horizontal axis represents time where the unit of time is the frame number of the frame of the video recording (discussed with reference to FIG. 6C) and the vertical axis represents distance in millimeters. The three curves x, y, and z shown on the graph represent the motion in the x, y, and z directions (as shown in FIG. 6C), respectively, of the joint(s) 646 or body part(s) circled 643 in FIG. 6D, that is, the motion that triggered the event selected from the list 610 in FIG. 6B. The user, e.g., clinician, may use the information provided in FIGS. 6B, 6D and 6E in addition to the video recording shown in FIG. 6C in determining whether to confirm or disconfirm an event (discussed above with reference to FIG. 6A). The clinician may also use the information provided in FIGS. 6B, 6D and 6E in addition to the video recording shown in FIG. 6C in determining whether and by how much to change a threshold for triggering an event (discussed above).

In some embodiments, the screenshot of FIG. 6B may indicate the particular type of abnormal event, that is, may indicate whether the abnormal event indicates a risk of fall or other medical event, or a diagnosis, risk, or decline with respect to a particular medical condition. The abnormal event type could be indicated (e.g., "At risk—fall," "At risk—arthritis," etc.) in the "Status" category or in an additional category that could be displayed, e.g., to the right of the "Status" category.

In some embodiments, the screenshot of FIG. 6B may indicate the level of risk/likelihood (of the given medical event or condition) reflected by the abnormal event. For example, different deviations from normal gait may indicate different levels of risk/likelihood of a particular medical event (e.g., fall) or condition. Specifically, larger deviations from normal gait (e.g., greater distance moved by a body part, see FIG. 6E) may indicate a higher risk of fall, a greater likelihood of having a given neurodegenerative condition, etc. This risk/likelihood level reflected by an abnormal event could be indicated by qualitative or quantitative indications of the level (e.g., "At risk—high," "At risk—moderate," and "At risk—low"; or "At risk—x," where x is an integer between 1 and 10, with 10 indicating the highest level of risk and 1 indicating the lowest level; etc.) in the "Status" category or in an additional category that could be displayed, e.g., to the right of the "Status" category.

The user interface 130, 231 may further be configured to permit the user to set the frequency at which the user is alerted to triggered events. For example, the user may be alerted every time an event is triggered, every time a certain number of events have been triggered, every time an event of a certain (abnormal event) type has been triggered, every time an event of a certain magnitude of abnormality has been triggered, once every day (or other fixed period of time), etc. Alternately, the user may set the system not to issue such alerts to the user, and the user may simply check the output from the system on a periodic, e.g., daily, basis. In addition, the system may be configured to send output to multiple users, e.g., a home health aide and a doctor, both of whom take care of the patient 140. Multiple user interface devices (see e.g., discussion of FIGS. 8 and 9 below) may be provided to the multiple users, respectively, for this purpose.

Figure 7:
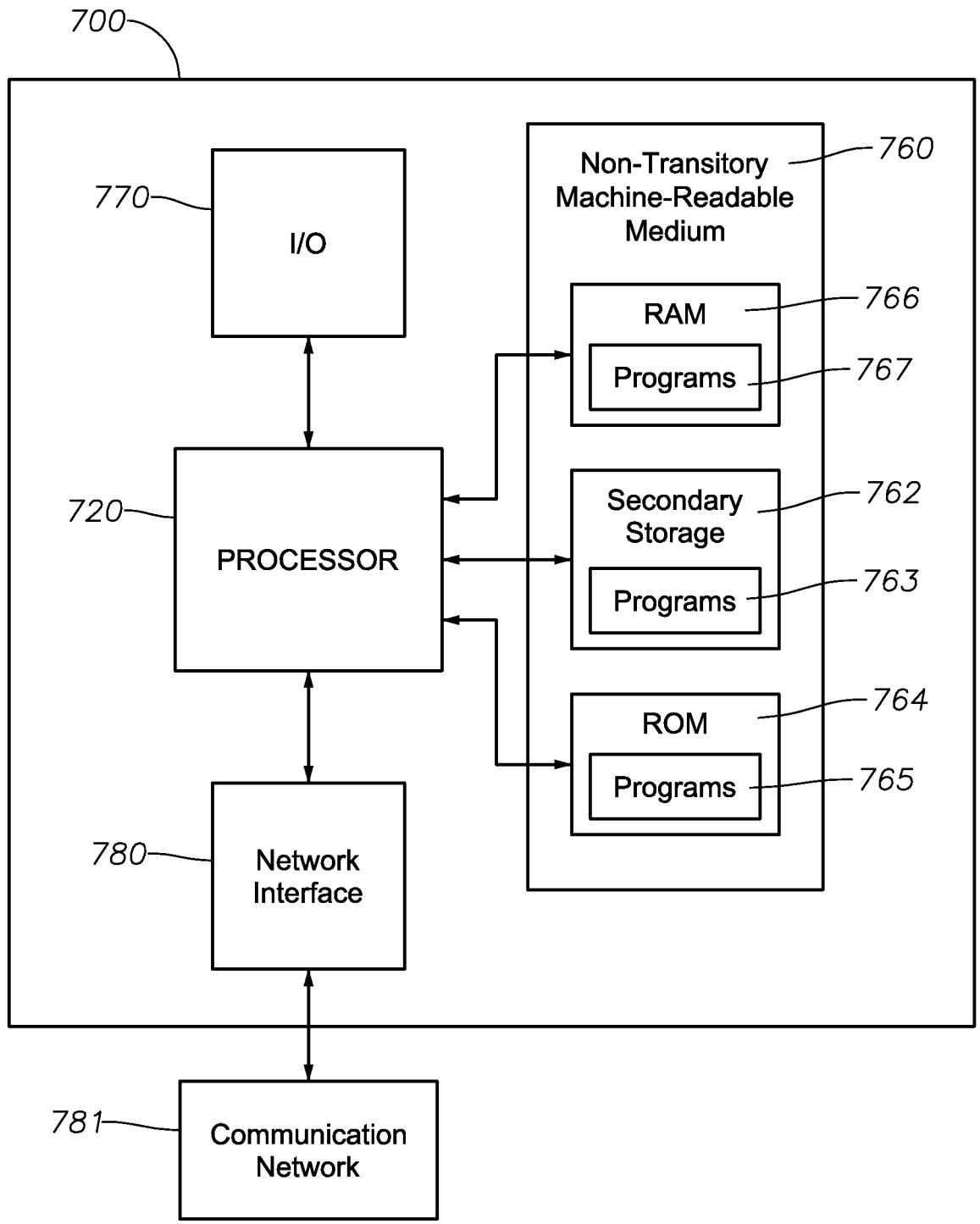
FIG. 7 is a block diagram of an exemplary computer system useful for implementing one or more embodiments.
Figure 8:
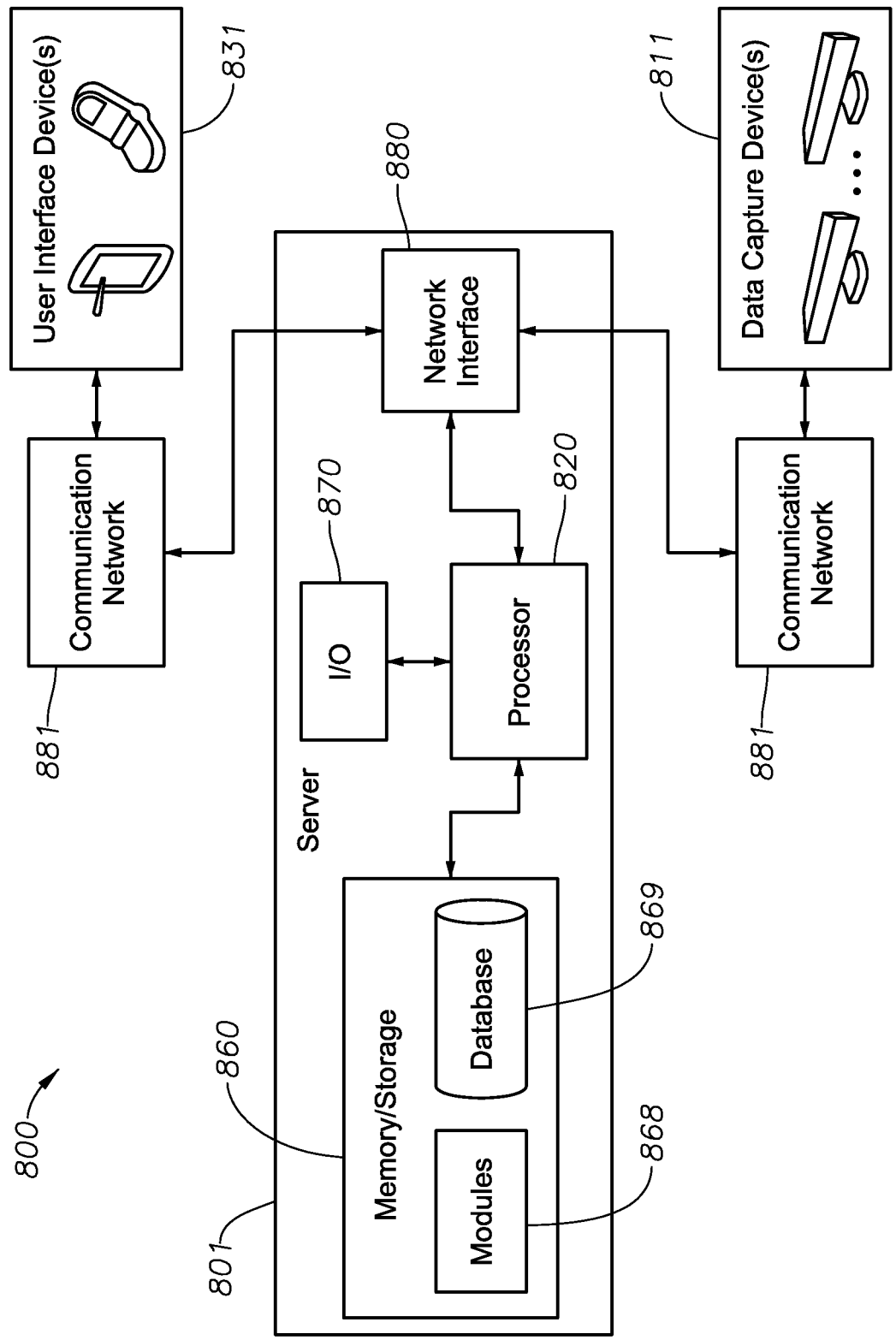
FIG. 8 is a block diagram illustrating a system for predicting medical events and conditions that are reflected in gait, according to some embodiments.
Figure 9:
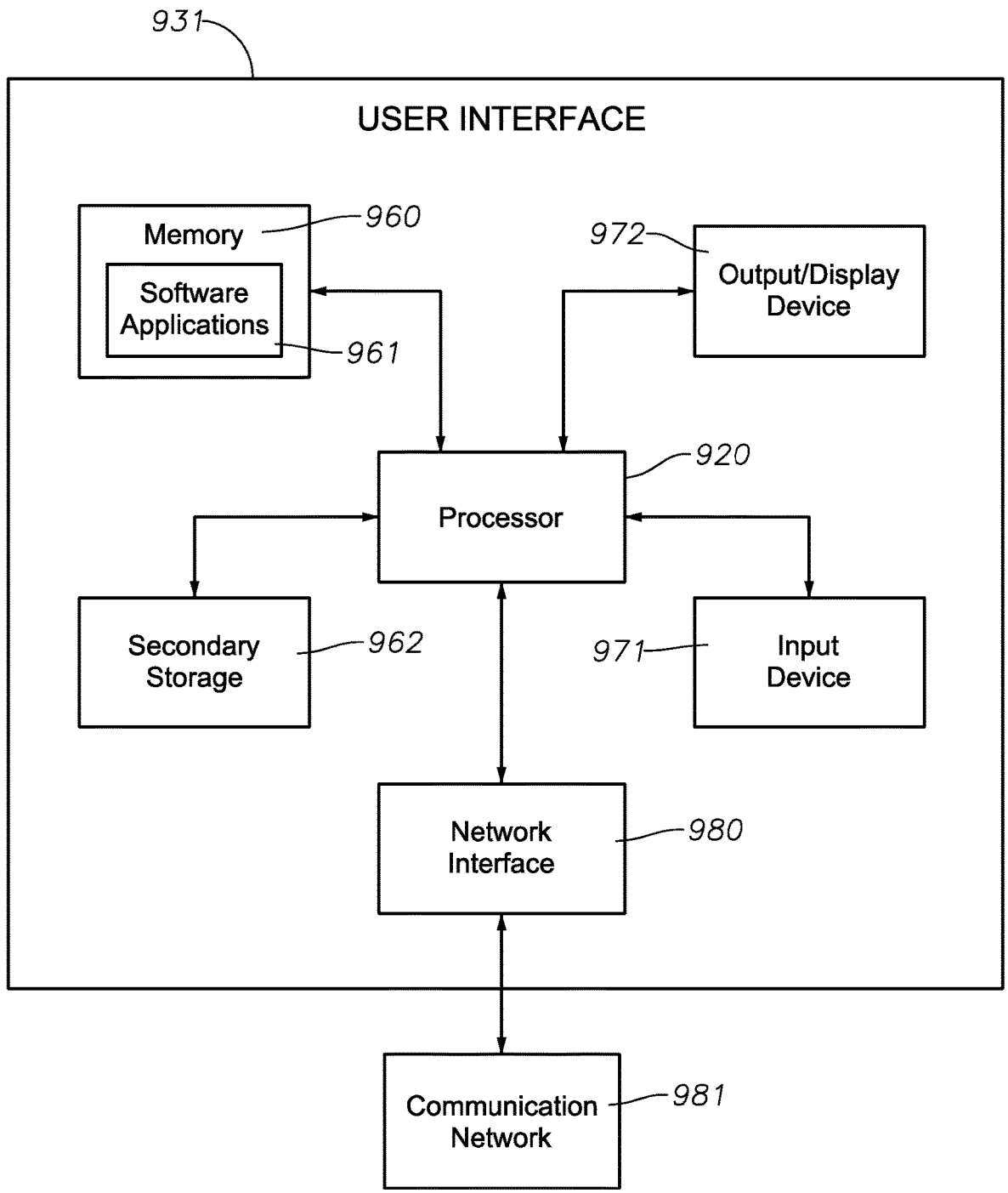
FIG. 9 is a block diagram of an exemplary computer system useful for implementing a user interface, according some embodiments.

FIGS. 7-9 are block diagrams illustrating a system (or portions thereof) for predicting medical events and conditions that are reflected in gait, according to some embodiments. While FIGS. 1-3 highlight the logical elements of such a system and their interconnections, FIGS. 7-9 highlight the computer hardware and communication network elements of such a system and their interconnections. In view of the different emphases and purposes of FIGS. 7-9 as compared with FIGS. 1-3, it will be understood that FIGS. 7-9 do not encompass all aspects or features of FIGS. 1-3, and FIGS. 1-3 do not encompass all aspects or features of FIGS. 7-9. In FIGS. 7-9, the double-headed arrows indicate the bidirectional operational and/or communicative interconnections between the elements, as will be understood by one of ordinary skill in the art in view of the instant disclosure. In FIGS. 1 and 2, the single-headed arrows indicate the flow or transmission (or capture) of information or data, as will be understood by one of ordinary skill in the art in view of the instant disclosure.

FIG. 7 is a block diagram of an exemplary computer system useful for carrying out some or all of the functionality of one or more embodiments described herein. As seen in FIG. 7, a computer system 700 includes at least one processor 720, which may be a programmable control device that may be programmed to perform steps or processes described herein. Such a processor may be referred to as a central processing unit (CPU) and may be implemented as one or more CPU and/or GPU (Graphics Processing Unit) chips. Computer system 700 also includes input/output (I/O) devices 770, network connectivity (or network interface) devices 780, and a non-transitory machine-readable medium 760, which may be a non-transitory computer-readable medium. Processor 720 is in communication with these other elements 760, 770 and 780.

The network connectivity or network interface devices 780 may include modems, modem banks, Ethernet cards, universal serial bus (USB) cards, serial interfaces, token ring cards, fiber distributed data interface (FDDI) cards, wireless local area network (WLAN) cards, radio transceiver cards such as code division multiple access (CDMA) and/or global system for mobile communications (GSM) radio transceiver cards, or other network devices. These network connectivity/interface devices 780 may enable the processor 720 to communicate with the Internet or one or more intranets or other communication networks, designated generally by reference numeral 781. With such a network connection, the processor 720 may transmit information to and receive information from other entities, via the network 781, in the course of performing steps or processes disclosed herein. This aspect of the system is further described below with reference to FIG. 8.

The I/O devices 770 may include printers, monitors, displays, speakers, speech synthesizers, touch screens, keyboards, keypads, switches, dials, mice, microphones, voice recognition devices, card readers, tape readers, or other input or output devices.

The machine-readable medium 760 may comprise memory devices including secondary storage 762, read only memory (ROM) 764, and random access memory (RAM) 766. The secondary storage 762 may include any form of optical or magnetic storage including solid-state storage, such as magnetic disks (fixed, floppy, and removable) and tape; optical media such as CD-ROMs and digital video disks (DVDs); and semiconductor memory devices such as Electrically Programmable Read-Only Memory (EPROM), Electrically Erasable Programmable Read-Only Memory (EEPROM), Programmable Gate Arrays and flash devices. The secondary storage 762 may be used for non-volatile storage of data and may be used as an over-flow data storage device if the RAM 766 is not large enough to hold all working data. The secondary storage 762 may be used to store instructions or programs 763 that are loaded into the RAM 766 when such instructions or programs 763 are selected for execution. Execution of such instructions and programs 763 cause the processor 720 to perform any of the steps or processes described in this disclosure. The ROM 764 may also be used to store instructions or programs 765 and may be used to store data to be read by the processor 720 during program execution. The ROM 764 is a non-volatile memory device which typically has a small memory capacity relative to the larger memory capacity of the secondary storage 762. The RAM 766 is used to store volatile data and may also be used to store programs 767 or instructions. Access to both the ROM 764 and the RAM 766 is typically faster than to the secondary storage 762.

The processor 720 executes codes, computer programs (e.g., 763, 765, 767), and scripts that it accesses from secondary storage 762, the ROM 764, the RAM 766, or the network connectivity/interface devices 780. The terms "logic" and "module" as referred to herein relate to structure for performing one or more logical operations. For example, a module may comprise circuitry which provides one or more output signals based upon one or more input signals. Such circuitry may comprise a finite state machine that receives a digital input and provides a digital output, or circuitry which provides one or more analog output signals in response to one or more analog input signals. Such circuitry may be provided in an application specific integrated circuit (ASIC) or field programmable gate array (FPGA). Also, a module may comprise machine-readable instructions stored in a memory in combination with processing circuitry to execute such machine-readable instructions. However, these are merely examples of structures which may provide logic, and embodiments disclosed herein are not limited in this respect. Also, items such as applications, modules, components, etc. may be implemented as software constructs stored in a machine-readable storage medium (e.g., 760), and those constructs may take the form of applications, programs, subroutines, instructions, objects, methods, classes, or any other suitable form of control logic. Steps or processes described herein may thus be performed by software, hardware, firmware, or any combination of one or more of these.

With reference to FIGS. 1 and 2, the computer system 700 of FIG. 7 may be used to implement, e.g., the data analysis and output generation subsystem 120 (FIG. 1), and the multi-sensor calibration module 221, data processing and multi-sensor fusion module 222, data analysis (parameter extraction) module 223, and assessment module 224 (FIG. 2). According to some embodiments, the computer system 700 of FIG. 7 may also be used to implement the user interface 130, 231 (FIGS. 1, 2).

FIG. 8 is a block diagram illustrating a system for predicting medical events and conditions that are reflected in gait, according to some embodiments. As compared to FIG. 7, FIG. 8 presents a more comprehensive view of the system, while at the same time abbreviating or omitting some of the detail of FIG. 7. As compared to FIG. 7, FIG. 8 also highlights the communication network elements of the system.

As seen in FIG. 8, the system 800 includes a computer 801, which may be a server, one or more data capture devices 811, and one or more user interface devices 831, which may be client devices. As suggested by the server-client configuration, the system 800 may be used to monitor a number of patients 140 (FIG. 1) and interface with a number of users, with each user being associated with (e.g., assigned to monitor, provide medical care for, etc.) one or more particular patients 140.

The computer/server 801 may include a processor 820, memory/storage 860, input/output devices 870, and a network interface 880. The network interface 880 is configured for enabling the computer/server 801 to communicate with the data capture devices 811 and the user interface devices 831 via a communication network 881, e.g., to receive captured data from the data capture devices 811, and to provide output to and receive feedback from the user interface devices 831. (While two boxes labeled "communication network 881" are depicted in FIG. 8, these boxes may be understood as representing a single communication network or multiple communication networks.) The communication network(s) 881 may include any one or more of a wired network, a wireless network (e.g., Wi-Fi network or cellular network), and facilities for data transmittal over telecommunications networks and services, and the network interface 880 may include appropriate corresponding interfaces. Communication over the communication network(s) 881 may occur in real-time when network connectivity is available. Alternatively, or when network connectivity is not available for immediate transmission, the data for transmission over the network 881 may be stored locally in memory/storage 860 and transmitted at a later time.

The processor 820, memory/storage 860, and input/output devices 870 may be identical or comparable to processor 720, non-transitory machine-readable medium 760, and input/output devices 770, which have been described with reference to FIG. 7. For brevity, however, the elements of memory/storage 860 are shown in a collapsed or abbreviated manner in FIG. 8. As described above, modules 868 may be software loaded into memory/storage 860, as shown in FIG. 8, but may also be implemented in hardware or firmware. Memory/storage 860 may also include one or more databases 869, which may be used to store, e.g., training data 250 (FIG. 2) and/or generated output data.

FIG. 9 is a block diagram of an exemplary computer system useful for implementing a user interface (e.g., 831), according to some embodiments. According to some embodiments, the user interface device may be implemented using the same computer (e.g., 700 of FIG. 7) as used to implement the data analysis and output generation subsystem 120 (or their correlates in FIG. 2). However, the user interface may also be implemented by a separate computer device, as illustrated in FIGS. 8 and 9.

As shown in FIG. 9, a user interface device 931 may include the following components: a processor 920, a memory 960, secondary storage 962, an input device 971, an output/display device 972, and a network interface 980 (as for each of these components, the user interface device 931 may include one or more of the given component, e.g., one or more input devices 971, one or more output/display devices 972, etc.). A general description of these elements (920, 960, 962, 971, 972, 980) of the user interface device 931 has been provided by the description of the same or analogous/similar elements (720, 760, 762, 764, 766, 770, 780) in FIG. 7. As seen in FIG. 9, software applications 961 may be loaded into the memory 960. Such software applications 961 may include the above-mentioned software application for implementing the user interface described above, which is defined in part by the screenshots (shown in FIGS. 6A-6E) described above. In the above-described user interface, the screenshots may be displayed on the output/display device 972, and the user may interact with the user interface device 931 via the input device(s) 971. Such interaction may involve, e.g., selecting output (e.g., 'events'), viewing output (video recordings of events, etc.), providing feedback (e.g., confirming/disconfirming events), and instructing the system to record data, as described above. Input devices 971 that may be provided on the user interface device 931 to facilitate such interactions may include a keyboard, a stylus, a touchscreen, etc. The network interface 980 is configured for enabling the user to communicate with (e.g., transmit information to and receive information from) other elements of the system (e.g., 800, FIG. 8) and entities external to the system, via a communication network 981. Such communications, elements, and entities have been described herein. Entities external to the system may include, e.g., the patient (140) being monitored, or medical personnel or institutions (other than the user), who may be notified/instructed to intervene medically on behalf of the patient 140, etc.

The user interface device 931 may be a mobile (e.g., client) device or a web (e.g., client) device. Mobile devices are electronic devices that are portable or mobile and include, e.g., mobile phones, such as smartphones (e.g., iPhones™, Android™ phones, Windows™ phones, BlackBerry™ smartphones), tablets (e.g., iPads™, Android™, Microsoft Surface™ tablets), etc. Web devices are electronic devices that are not considered (as) portable or mobile as mobile devices and include, e.g., personal computers, such as laptop and desktop computers, etc. As discussed, the user interface device 931 may (but need not) be remote from other elements of the system.

After reading the description presented herein, it will become apparent to a person skilled in the relevant arts how to implement embodiments disclosed herein using computer systems/architectures and communication networks other than those described herein.

As reflected by FIGS. 7-9, it will be understood that a system for predicting medical events and conditions that are reflected in gait may include any one or more of the three subsystems (110, 120, 130) shown in FIG. 1. For example, such a system may include a data capture subsystem 110, which may operate with a data analysis/output generation subsystem 120 that is separate from the system. Such system may include a user interface 130, or may operate with a user interface 130 that is separate from the system. As another example, such a system may include a data analysis/output generation subsystem 120, which may operate with a data capture subsystem 110 that is separate from the system. Such system may include a user interface 130, or may operate with a user interface 130 that is separate from the system. As another example, such a system may include a user interface 130, which may operate with a data analysis/output generation subsystem 120 that is separate from the system. Such system may include a data capture subsystem 110, or may operate with a data capture subsystem 110 that is separate from the system.

Systems and methods disclosed herein provide advantages relative to the prior art. For example, such systems and methods may employ as data capture devices multiple cameras or sensors, including some stationary cameras at fixed locations in the patient's environment and at least one mobile camera that automatically tracks the moving patient. As such, such systems and methods do not require use of markers worn on the patient. This arrangement makes it less burdensome and intrusive for the patient as compared to markers that are worn by the patient. This arrangement also permits and facilitates monitoring a patient at home, in a normal living environment, while the patient engages in normal activities, which may involve the patient moving about. Thus, this arrangement permits and facilitates unobtrusive, continuous gait monitoring. Finally, this arrangement increases accuracy of data capture, accumulating less error compared to prior art systems and methods that use fewer imaging devices and do not use a mobile imaging device.

As another example, the systems and methods disclosed herein are low cost, by virtue of using relatively inexpensive data capture devices designed for use by the ordinary consumer, such as the Microsoft™ Kinect camera or the ASUS™ XTion™ camera, rather than devices such as the Vicon™ motion capture system, which are priced for institutional use. Further, the systems and methods have been tested for accuracy against the Vicon™ system as ground truth, and the systems and methods compared favorably to Vicon™, as detailed in the aforementioned article, "Evaluating the Accuracy of a Mobile Kinect-based Gait-Monitoring System for Fall Prediction."

As another example, the elimination of markers and the use of the calibration method described above make the systems and methods disclosed herein usable by a layman, in contrast to prior art systems and methods that require technical expert involvement in calibrating imaging devices and in placing markers on the patient.

As another example, the systems and methods disclosed herein provide user-friendly output. As seen in the description of the screenshots (FIGS. 6A-6E) of the user interface, the results provided to the user (e.g., health care provider) are easy to understand, and are convenient and not time-consuming to access. The user is provided with simple, straightforward results. For example, while the systems and methods may video record the patient continually or over long periods of time, the systems and methods present to the user short video recordings of abnormal events for the user to selectively view instead of the user having to review long amounts of video (see discussion with reference to FIG. 6C). As another example, the user can quickly identify 'at risk' events (see discussion with reference to FIG. 6B), the body parts whose motion triggered an 'at risk' event (see discussion with reference to FIG. 6D), and the extent of motion of those body parts (see discussion with reference to FIG. 6E). The results provided to the user are both quantitative (e.g., identification of the body parts triggering the abnormal event; extent of motion of the body parts that triggered the event) and qualitative (e.g., basic medical conclusion—evaluation of event as 'normal" or 'at risk', evaluation of event as precursor of particular type of medical event/condition; video recording of abnormal event). Because the user can understand the significance of the output immediately, without having to pore over a detailed report, the user may be able to respond to the output, e.g., trigger necessary medical intervention, more quickly than prior art systems and methods that do not provide results in such user-friendly formats.

In addition, because the patient has the option of permitting the user to view the actual video recording or merely a filtered version thereof, the patient has the ability to maintain his/her privacy.

The systems and methods disclosed herein also provide a user-friendly way for the user to provide feedback to the system as to verification of the events; the user can quickly view the video recording of an event and confirm or disconfirm the event (see discussion with reference to FIGS. 6B, 6C). This will encourage the provision of verification feedback by the user, which may increase the extent to which performance of the systems and methods improves.

Finally, the increased extent of automation of the systems and methods disclosed herein as compared to prior art systems and methods may improve performance and make the systems and methods more user-friendly. For example, as described above, the need for technical expert involvement is eliminated or reduced in the matter of calibration and installation of data capture devices, and the output is rendered to the user in a format that is easily accessible and understandable, without requiring the user to exert effort to access the output or to perform analysis to understand the output.

In light of the principles and example embodiments described and illustrated herein, it will be recognized that the example embodiments can be modified in arrangement and detail without departing from such principles. Also, the foregoing discussion has focused on particular embodiments, but other configurations are also contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise or so dictated by the description herein.

Similarly, although example methods or processes have been described with regard to particular steps or operations performed in a particular sequence, numerous modifications could be applied to those methods or processes to derive numerous alternative embodiments of the present invention. For example, alternative embodiments may include methods or processes that use fewer than all of the disclosed steps or operations, methods or processes that use additional steps or operations, and methods or processes in which the individual steps or operations disclosed herein are combined, subdivided, rearranged, or otherwise altered. Similarly, this disclosure describes one or more embodiments wherein various operations are performed by certain systems, applications, module, components, etc. In alternative embodiments, however, those operations could be performed by different components. Also, items such as applications, module, components, etc. may be implemented as software constructs stored in a machine accessible storage medium, such as an optical disk, a hard disk drive, etc., and those constructs may take the form of applications, programs, subroutines, instructions, objects, methods, classes, or any other suitable form of control logic; such items may also be implemented as firmware or hardware, or as any combination of software, firmware and hardware, or any combination of any two of software, firmware and hardware. The term "processor" may refer to one or more processors.

Further, each of the method embodiments set forth above, including all combinations of method embodiments, may also be instantiated as an article of manufacture embodiment, wherein an article of manufacture comprises a non-transitory machine-accessible medium containing instructions, the instructions comprising a software application or software service, wherein the instructions, when executed by the machine, cause the machine to perform the respective method. The machine may be, e.g., a processor, a processor-based system such as the systems described herein, or a processor-based device such as the user interface device described herein (see, e.g., discussion with reference to FIG. 9).

What is claimed is:

1. A system for predicting medical events and conditions reflected in gait, comprising:
 a data capture subsystem comprising multiple calibrated video cameras configured to capture video data pertaining to the gait of a patient as the patient walks;
 a data analysis and outcome generation subsystem configured to:
  fuse the captured video data from the video cameras,
  extract gait parameters from the fused video data including a position and a velocity of an anthropometric center of mass of the patient,
  determine (a) a likelihood of the patient falling and (b) a likelihood of the patient having a neurodegenerative condition, where the determination of the likelihoods uses the extracted gait parameters and a machine learning algorithm trained on training data comprising gait parameters of population data from both persons with a normal gait and persons with an abnormal gait, and
  generate an output comprising the determination of the likelihoods and a segment of the video data that illustrates an abnormal gait event that is indicative of the determined likelihood of the patient falling or having a neurodegenerative condition; and
 a user interface subsystem configured to provide the output to a user and to receive feedback from the user comprising verification that confirms or disconfirms occurrence of the abnormal gait event, wherein the extracted gait parameters and corresponding feedback from the user are added to the training data.

2. The system according to claim 1, wherein the feedback from the user further comprises a notification to the patient.

3. The system according to claim 1, wherein the feedback from the user further comprises instructions for medical intervention.

4. The system according to claim 1, wherein the multiple video cameras include at least one fixed video camera and at least one mobile video camera configured to follow the patient as the patient walks.

5. The system according to claim 1, wherein the output further comprises identification of a degree of likelihood of the patient experiencing a fall or having a neurodegenerative condition.

6. The system according to claim 1, wherein the segment of the video data comprises actual video data of an abnormal gait event of the patient.

7. The system according to claim 1, wherein the segment of the video data comprises filtered video data of an abnormal gait event of the patient.

8. The system according to claim 1, wherein the output further comprises indication of an extent of deviation of the patient's gait from a normal gait of a sample population.

9. The system according to claim 1, wherein the output further comprises identification of particular body part(s) of the patient that manifested a deviation that triggered the data analysis and outcome generation subsystem to identify an abnormal gait event of the patient.

10. The system according to claim 1, wherein the data analysis and outcome generation subsystem is configured to determine the likelihood of the patient falling and the likelihood of the patient having a neurodegenerative condition based solely on the following extracted gait parameters: position and velocity of the anthropometric center of mass of the patient, anteroposterior and mediolateral angles of the patient, and knee angles of the patient.

11. The system of claim 1, wherein the training data further comprises historical data of the patient and the assessment is based on the evaluation of the extracted gait parameters compared to the historical data of the patient.

12. The system of claim 1, wherein the determination of likelihoods using the extracted gait parameters comprises a threshold for at least one gait parameter.

13. The system of claim 12, wherein the threshold of the at least one gait parameter can be adjusted by a user based on a history of the patient.

14. A method for predicting medical events and conditions reflected in gait, comprising:

capturing, using multiple calibrated video cameras, video data pertaining to the gait of a patient as the patient walks;

fusing the captured video data from the video cameras;

extracting gait parameters from the fused video data including a position and a velocity of an anthropometric center of mass of the patient;

determining (a) a likelihood of the patient falling and (b) a likelihood of the patient having a neurodegenerative condition, where the determination of the likelihoods uses the extracted gait parameters and a machine learning algorithm trained on training data comprising gait parameters of population data from both persons with a normal gait and persons with an abnormal gait;

generating an output comprising the determination of the likelihoods and a segment of the video data that illustrates an abnormal gait event that is indicative of the determined likelihood of the patient falling or having a neurodegenerative condition;

providing the output to a user; and receiving feedback from the user including verification that confirms or disconfirms occurrence of the abnormal gait event, wherein the extracted gait parameters and corresponding feedback from the user are added to the training data.

15. The method according to claim 14, wherein the feedback from the user further comprises a notification to the patient or instructions for medical intervention.

16. The method according to claim 14, wherein the multiple video cameras include at least one fixed video camera and at least one mobile video camera configured to follow the patient as the patient walks.

17. The method according to claim 14, wherein determining the likelihood of the patient falling and the likelihood of the patient having a neurodegenerative condition is based solely on the following extracted gait parameters: position and velocity of the anthropometric center of mass of the patient, anteroposterior and mediolateral angles of the patient, and knee angles of the patient.

* * * * *